(12) United States Patent
Khanna

(10) Patent No.: US 11,938,055 B2
(45) Date of Patent: Mar. 26, 2024

(54) METHOD AND APPARATUS FOR TREATING THE BRAIN AND/OR SPINAL CORD USING A CATHETER

(71) Applicant: Rohit Khanna, Daytona Beach, FL (US)

(72) Inventor: Rohit Khanna, Daytona Beach, FL (US)

(\*) Notice: Subject to any disclaimer, the term of this patent is extended or adjusted under 35 U.S.C. 154(b) by 348 days.

(21) Appl. No.: 17/075,058

(22) Filed: Oct. 20, 2020

(65) Prior Publication Data

US 2021/0030587 A1 Feb. 4, 2021

Related U.S. Application Data

(63) Continuation of application No. 16/131,405, filed on Sep. 14, 2018, now Pat. No. 10,849,787.

(Continued)

(51) Int. Cl.
*A61F 7/12* (2006.01)
*A61M 1/00* (2006.01)
(Continued)

(52) U.S. Cl.
CPC ............... *A61F 7/12* (2013.01); *A61F 7/123* (2013.01); *A61M 1/85* (2021.05); *A61M 19/00* (2013.01); *A61M 25/0026* (2013.01); *A61M 25/003* (2013.01); *A61F 2007/0056* (2013.01); *A61F 7/0085* (2013.01); *A61F 2007/0096* (2013.01); *A61F 2007/126* (2013.01); *A61M 3/0229* (2013.01); *A61M 2025/0024* (2013.01); *A61M 2025/0031* (2013.01); *A61M 2027/004* (2013.01); *A61M 27/006* (2013.01);
(Continued)

(58) Field of Classification Search
CPC .............. A61F 7/12; A61F 2007/126; A61F 2007/0056; A61F 2007/0054; A61M 27/006; A61M 27/004
See application file for complete search history.

(56) References Cited

U.S. PATENT DOCUMENTS

| 4,904,237 A | 2/1990 | Janese |
| 6,217,552 B1 * | 4/2001 | Barbut ............... A61M 27/006 604/113 |

(Continued)

FOREIGN PATENT DOCUMENTS

CN 203915575 U * 11/2014

OTHER PUBLICATIONS

Machine Translation of CN 203915575 U (Year: 2014).*

*Primary Examiner* — Laura A Bouchelle
(74) *Attorney, Agent, or Firm* — Wenderoth, Lind & Ponack, L.L.P.

(57) ABSTRACT

A method for treatment of a brain and/or spinal cord includes inserting a flexible catheter into a cerebrospinal fluid space, the flexible catheter including two lumens adapted to allow a fluid to circulate therein in a closed loop within the flexible catheter and the flexible catheter being adapted to be connected to a device for cooling and circulating the fluid. The cerebrospinal fluid in the cerebrospinal fluid space is cooled with the flexible catheter to enable selective central nervous system cooling. The functional status of the brain and/or spinal cord is monitored, and the treatment of the brain and/or spinal cord is modified to adjust for any change in the functional status of the brain and/or spinal cord.

18 Claims, 22 Drawing Sheets

Related U.S. Application Data

(60) Provisional application No. 62/559,168, filed on Sep. 15, 2017.

(51) Int. Cl.
  A61M 19/00 (2006.01)
  A61M 25/00 (2006.01)
  *A61F 7/00* (2006.01)
  *A61M 3/02* (2006.01)
  *A61M 27/00* (2006.01)

(52) U.S. Cl.
  CPC ............... *A61M 2202/0464* (2013.01); *A61M 2205/3303* (2013.01); *A61M 2205/3344* (2013.01); *A61M 2205/3606* (2013.01); *A61M 2205/366* (2013.01); *A61M 2210/0693* (2013.01); *A61M 2210/1003* (2013.01); *A61M 2230/08* (2013.01); *A61M 2230/10* (2013.01); *A61M 2230/30* (2013.01); *A61M 2230/50* (2013.01)

(56) References Cited

U.S. PATENT DOCUMENTS

| | | | |
|---|---|---|---|
| 6,379,331 B2 | 4/2002 | Barbut et al. | |
| 6,527,798 B2 | 3/2003 | Ginsburg et al. | |
| 6,699,269 B2 | 3/2004 | Khanna | |
| 6,758,832 B2 | 7/2004 | Barbut et al. | |
| 6,929,656 B1 | 8/2005 | Lennox | |
| 7,004,961 B2 | 2/2006 | Wong et al. | |
| 7,144,418 B1 | 12/2006 | Lennox | |
| 7,318,834 B2 * | 1/2008 | Njemanze | A61F 7/12 607/105 |
| 7,842,002 B2 * | 11/2010 | Mantle | A61M 3/0258 604/6.11 |
| 8,123,789 B2 | 2/2012 | Khanna | |
| 2012/0221082 A1 | 8/2012 | Khanna | |
| 2017/0095649 A1 * | 4/2017 | Vase | A61F 7/123 |

\* cited by examiner

*Achieved with catheter

ICP = Intracranial pressure

CPP = Cerebral perfusion pressure (CPP = Mean arterial pressure − ICP)

EEG = Electroencephalography

SSEP = Somatosensory evoked potential

MEP = Motor evoked potential

FIG. 29

| Neurologic Monitoring Parameter | Decrease ICP with CSF Drainage* | Decrease Temperature* | Increase Coolant Circulation Rate* | Decrease Coolant Temperature* | Increase CPP[1] | ICP Medications[2] | Surgical Maneuver |
|---|---|---|---|---|---|---|---|
| ICP Increase | YES → | YES → | YES → | YES → | YES → | YES → | YES[3] |
| Temperature Increase | NO | YES → | YES → | YES | NO | NO | NO |
| CPP Decrease | YES → | YES → | YES → | YES → | YES → | YES → | YES[3] |
| EEG Change | YES → | YES → | YES → | YES → | YES → | YES → | YES[3] |
| SSEP Change | YES → | YES → | YES → | YES → | YES → | YES → | YES[4] |
| MEP Change | YES → | YES → | YES → | YES → | YES → | YES → | YES[4] |
| D wave Change | YES → | YES → | YES → | YES → | YES → | YES → | YES[4] |

*Achieved with catheter

[1] Increase mean arterial pressure with intravascular fluids, blood transfusion, ionotropic medications

[2] Hyperosmolar agents, hypertonic saline, barbiturates, propofol, muscle paralytics, pentobarbitol

[3] Decompressive Craniectomy

[4] Halt or abort aortic or spinal surgery; re-anastomose disrupted intercostal/radicular arteries from the aorta to the spinal cord.

METHOD AND APPARATUS FOR TREATING THE BRAIN AND/OR SPINAL CORD USING A CATHETER

BACKGROUND

The current disclosure relates to brain and spinal cord disease treatment. The disclosure more specifically relates to a method and apparatus for protecting the brain and spinal cord by selectively altering the temperature of the central nervous system and/or draining cerebrospinal fluid (CSF).

Central nervous system diseases like trauma, stroke, hemorrhage, tumors, infection, surgery, etc. frequently lead to brain and/or spinal cord swelling and an increase in the central nervous system pressure. An increased central nervous system pressure, in turn, decreases the cerebral perfusion pressure and, consequently, the blood flow which further exacerbates the neurologic condition.

Aortic operations of the thoracic and abdominal aorta are not infrequently complicated by paraplegia. Paraplegia after thoracic aortic aneurysm surgery is a devastating condition with high morbidity and poor quality of life, as well as mortality. Spinal ischemia following aortic surgery is also a well-known complication. During thoracic or abdominal aortic aneurysm/dissection repair, the intercostal/radicular arteries supplying blood to the spinal cord from the aorta, especially the Artery of Adamkiewicz, can be disrupted or occluded impairing the blood flow to the spinal cord. Aortic clamping to facilitate aneurysm repair can also result in a reduction of spinal cord perfusion, especially if the clamp time is longer than, for example, 45 minutes, which often results in paralysis.

Hypothermia has been shown to provide cerebral and spinal cord injury protection from trauma, ischemia, or hypoxia. Ischemia may occur from cardiac arrest, cardiac failure, stroke, head or spinal cord injury, aneurysm surgery, cardiac surgery, aortic dissection or aneurysm treatment or carotid surgery. Hypothermia is also effective in reducing increased intracranial pressure from cerebral swelling. The mechanisms involved in hypothermic cerebral protection are several-fold and include, for example, 1) reducing cerebral glucose and oxygen metabolism and decreasing lactate content following injury, 2) preventing disruption of the blood brain barrier and consequently reducing cerebral edema, 3) reducing endogenously toxic neurotransmitters like glutamate, glycine, aspartate, acetylcholine, and norepinephrine that enter the brain after injury, 4) inhibiting excessive calcium entry and intracellular calcium overload into neurons, 5) protecting membrane structural proteins like microtubule-associated protein-2, and 6) preventing diffuse axonal injury following brain trauma.

In general, the human brain and spinal cord are maintained at a relatively constant temperature of approximately 37 to 38 degrees Celsius. Hypothermia is considered mild when the body temperature is 33 to 35 degrees Celsius, moderate in the temperature range of 28 to 33 degrees Celsius, and severe in the temperature range of 24 to 28 degrees Celsius. Most studies in humans have involved mild to moderate systemic hypothermia mainly because of the significant side effects that occur from induced systemic hypothermia. These include infection, cardiac arrhythmias, coagulopathy, renal failure, pneumonia, excessive shivering, as well as rewarming shock. In order to avoid these complications, the degree and duration of induced hypothermia have been relatively short, thereby limiting its effectiveness.

Generally, in the past, cooling of the brain and/or spinal cord has been accomplished through whole body cooling by, for example, using a cooling blanket, immersing the patient in an ice bath, or cooling the blood through a cardiopulmonary bypass machine. A few methods have been described regarding selective brain and spinal cord hypothermia. These involve cooling the arterial vessel or blood supply to the brain or using external cooling helmets, each with its own significant limitations.

Several catheters have been developed to induce systemic hypothermia by inserting them into the bloodstream. More recently, catheters have been developed that can be inserted into the arterial vessels to the brain to induce selective brain hypothermia. These catheters are limited in their size and functionality by their small vessel lumen, as well the inability to cool all four major arterial vessels supplying blood to the brain, and are unable to cool the spinal cord via this methodology. They also carry the risk of ischemic and thromboembolic stroke by either impairing the blood flow to the brain or dislodging clots that can develop in intra-arterial catheters.

External cooling helmets have limited effectiveness since the blood supply to the cooled scalp does not circulate into the brain and returns systemically, which, along with the thickness of the skull, dilutes the hypothermic effect to the brain.

Selective brain and spinal cord cooling by the insertion of closed loop system catheters into the ventricular, subdural or epidural space was first described in U.S. Pat. No. 6,699,269 to Khanna. It also describes a catheter that expands with the circulation of a coolant in the closed loop system within the central nervous system. This avoids the side effects and complications seen from other methods of cooling. It also circumvents infection and fluid overload [with exacerbation of, which can exacerbate brain swelling that can be potentially encountered with cooling systems involving directly circulating a coolant into the cerebrospinal fluid space inside the skull or spinal canal. The Khanna U.S. Pat. No. 6,699,269 patent also relates to cerebrospinal fluid drainage to relieve an increase in intracranial pressure (ICP). U.S. Pat. No. 8,123,789 and U.S. Application Publication No. 2012/0221082 by Khanna also relate a method and apparatus for selective central nervous system cooling with a balloon catheter. The balloon can be expanded to increase the surface area that contacts the cerebrospinal fluid and the brain or spinal cord to facilitate heat exchange.

Past devices and systems lack specificity in the operational mechanism for the treatment of central nervous system disease. They relate to cooling the whole body with external pads, intravascular cooling or cooling with a helmet. These systemic cooling approaches are countered by the body's own mechanisms of thermoregulation and, therefore, are ineffective or achieve very minimal effects. As an alternative to systemic cooling, selective central nervous system hypothermia by circulating a coolant in the cerebrospinal fluid space or directly cooling the central nervous system with a closed loop catheter with or without a balloon has been utilized.

Other past devices and methods relate to indiscriminate central nervous system cooling and cerebrospinal fluid drainage for the treatment of central nervous system disease, but lack any specificity in the methodology for optimizing the neurologic outcome.

Therefore, there is a need for an apparatus and method with high specificity based on feedback from neurologic monitoring parameters and acting directly on the brain and/or spinal cord by thermal exchange with the CSF for relieving central nervous system pressure, increasing blood flow, reducing metabolic rate and resetting thermoregulation.

SUMMARY

The present disclosure relates to an apparatus and method for specific and discriminate treatment of central nervous system disease based on feedback from neurologic monitoring parameters. This is achieved by performing selective hypothermia to the brain and/or the spinal cord for injury protection without the need for systemic cooling, as well as providing drainage of any excess cerebrospinal fluid through the apparatus.

Past devices and methods based on indiscriminate and non-specific treatment fail to achieve a high level of the central nervous system disease treatment. For instance, they do not consider associating the degree of hypothermia with the extent of neurologic deficit prevention.

Generally speaking, hypothermia induction with a temperature between 24-28 degrees Celsius can provide better neurologic protection as compared to a temperature between 33-35 degrees Celsius.

The extent of central nervous system or intracranial pressure decrease is associated with decreased neurologic deficits and it is desirable to keep the ICP at, for example, less than 20 mmHg or at, for example, less than 10 mmHg. ICP reducing measures include the extent of CSF drainage, degree of hypothermia, decreasing cerebral/spinal cord edema, decreasing central nervous system blood volume, reducing neuronal metabolism, and improving central nervous system blood flow. ICP reduction can be accomplished by adjusting the amount of cerebrospinal fluid drainage, as well the temperature of the central nervous system.

Medications like mannitol, hyperosmolar therapy, and hypertonic saline also decrease brain or spinal cord edema by removing excess fluid through an osmotic effect and reduce elevated ICP. ICP reduction by reducing the brain/spinal cord metabolism can also be accomplished with medications like barbiturates, propofol, and pentobarbitol. The ICP can be monitored, for example, through sensors in the catheter, an external pressure transducer connected to the catheter drainage lumen, and/or by free drainage, which involves maintaining the external CSF drain reservoir/bag at a 10 mmHg level or any other desired level. For example, maintaining the drainage reservoir at 13 cm above the external auditory meatus equates to 10 mmHg pressure and an ICP above this limit will be treated by free flowing CSF drainage until this pressure is achieved.

Maintaining an adequate blood pressure and particularly the cerebral perfusion pressure (CPP) in a desirable range improves central nervous system blood flow and is associated with a better neurologic outcome and a CPP between 50-80 mmHg has been shown to be very effective in maintaining neurologic function. CPP below 50 mmHg can lead to ischemia and CPP higher than 80 mmHg can promote hyperemia, especially in an injured brain, and increase ICP.

Somatosensory evoked potentials (SSEP) can be used to monitor central nervous system function. Large diameter, myelinated and fast conducting cutaneous and muscle afferents carry the peripheral SSEP. SSEP can be used to monitor the dorsal column-medial lemniscus pathway, which mediates tactile discrimination, vibration sensation, form recognition and joint/muscle sensation (conscious proprioception). In SSEP monitoring, stimulation electrodes excite controlled repetitive action potentials that propagate from peripheral nerves to the contralateral sensory cortex through the dorsal roots and the dorsomedial tracts of the spinal cord. These signals can be recorded at various anatomically accessible locations, such as the peripheral nerve, spinal cord, brainstem and its endpoint, and the somatosensory cortex. Subdermal needle electrodes can be used for both stimulation and recording.

Cortical spinal cord evoked potential and direct wave (D Wave) spinal cord stimulation and recording can also provide functional monitoring of the corticospinal tract.

Neurogenic motor evoked potential (MEP) is an elicited potential that is electrically stimulated at the spinal cord with epidural electrodes and then recorded from the peripheral nerves. Neurogenic MEPs are recorded by stimulating the spinal cord through electrodes inserted by a surgical team. A flexible spinal electrode is inserted into the epidural space proximal to the operating field. The stimulation parameters can be as follows: Intensity: 20-50 mA; Duration of Stimulation: 1 ms; and Frequency: 4.1 Hz. Recordings can be performed, for example, at the internal popliteal sciatic nerves or the posterior tibial nerves. This technique allows monitoring of the overall spinal cord.

Neurogenic evoked potentials from peripheral nerves in lower extremities after spinal cord stimulation can be used to monitor spinal motor pathways. These potentials contain at least a significant antidromical sensory component. The biphasic component corresponds to antidromical activation of the sensory pathways, whereas the polyphasic component corresponds to activation of the motor pathways. Neurogenic MEPs provide combined sensory and motor spinal pathway monitoring.

Free-running electromyography (frEMG) with spontaneous activity can be recorded via needle electrodes placed in the muscles of interest. Relevant frEMG activity includes spikes, bursts, or trains, and the occurrence of neurotonic discharges can indicate nerve injury.

As noted above, MEP, SSEP, and D wave monitoring are methods for spinal cord monitoring. MEPs are elicited, for example, by transcranial magnetic stimulation or by placing electrodes on the scalp to produce transcranial electrical stimulation, which can be recorded, for example, via the epidural space or from peripheral limb muscles. For example, by maintaining a mean distal aortic pressure of 60 mmHg with left heart bypass, the MEPs usually can be maintained at adequate levels in most patients. In patients that have evidence of impaired spinal cord function, increasing distal aortic pressure is usually successful in restoring MEPs.

The monitoring of MEPs during surgery can also guide the physician in determining the optimum post-operative blood pressure. In patients who are at significant risk of spinal cord ischemia, serial cross-clamping of the aorta may identify the critical segments of the aorta that provide important blood supply to the spinal cord. MEPs may, therefore, be used to determine the need and position of intercostal and lumbar artery graft placement. In some patients, MEPs decrease significantly during aortic cross-clamping because of critical spinal cord ischemia, but usually return after spinal cord blood flow is restored. If the MEPs remain attenuated, it is likely that the patient will be left with a permanent neurological deficit.

SSEP monitoring may also be useful in detecting spinal cord ischemia. However, SSEPs only reflect the conduction of sensory information in the posterior column, which has a different blood supply from that supplying the motor system located in the anterolateral part of the spinal cord. Neurologic monitoring with MEPs and SSEP for the detection of spinal cord dysfunction can be performed because MEPs and SSEP are well correlated when intra-operative changes are irreversible and each method has a strong negative predictive value.

In order to avoid spinal cord ischemia in patients undergoing either surgical or endovascular treatment of aortic disease, several strategies are proposed to avoid this complication. These include drainage of cerebrospinal fluid, raising the systemic blood pressure with inotropic medications and intravascular volume, hypothermia, and re-anastomosis of the disrupted radicular blood vessels supplying blood from the spinal cord to the aorta. Electromyogram (EMG) and nerve conduction study (NCS) monitoring can also be used to monitor the function of cranial and peripheral nerves.

The advantage of spinal cord drainage with increased pressures can be seen when the spinal cord is monitored by methods described above. With the drainage of CSF there may be a dramatic reversal in spinal cord dysfunction as monitored by MEP and SSEP. Indeed, this monitoring method may be used to guide the extent of CSF drainage.

An electroencephalogram (EEG) is a noninvasive test that records electrical patterns in the brain. The test is used to help diagnose conditions such as seizures, epilepsy, head injuries, strokes, dizziness, headaches, brain tumors and sleeping problems. It can also be used to confirm brain death. EEG is also used to monitor cerebral function and metabolism. It is reliable in early detection of cerebral dysfunction especially due to ischemia and reduced oxygen delivery. Brain oxygenation monitoring can be undertaken with intracerebral or cerebrospinal fluid probes/sensors, as well as external scalp oxygen saturation monitors. Monitoring of the jugular venous oxygen levels can also indicate the level of brain oxygenation and indicate cerebral flow levels.

Previous methods lack adequate neurologic function monitoring parameters and interactive responsiveness and adjustment of the treatment in order to maintain a high level of neurologic function. Functional monitoring parameters include spinal cord evoked potentials, D-wave monitoring, arterial blood pressure, end-tidal partial pressure of carbon-dioxide, cerebral blood flow, Doppler blood flow velocity, intracranial or spinal intrathecal pressure, cerebral perfusion pressure, EEG, SSEP, MEP, corticography, brain oxygenation, and microdialysis probes monitoring metabolites. As a result, in previous methods, the level of hypothermia and the extent of cerebrospinal fluid drainage are not determined in response to the neurologic status of the patient, but is rather decided empirically. The rationale for a dynamic responsive system can be illustrated, for example, with the hemodynamic status after a head injury. In cases of head injury, ICP is a determinant of cerebral blood flow (CBF) because of its influence on the cerebral perfusion pressure (CPP) defined as the mean arterial blood pressure (MABP) minus the ICP.

A rise in CPP within the operative range of cerebral autoregulation results in compensatory active vasoconstriction to maintain a stable cerebral blood flow. The vasoconstriction leads to a decrease in cerebral blood volume and thereby to a decrease in intracranial pressure. Below the lower cerebral autoregulatory limit or with autoregulatory failure in some patients after head injury, an increase in cerebral perfusion pressure can result in passive vasodilatation, which can increase the cerebral blood volume and, therefore, the intracranial pressure. In this situation of cerebral autoregulatory failure, cerebral blood flow will vary with cerebral perfusion pressure, and stable blood flow may no longer be maintained. What is desired is a treatment methodology that relates to ICP and CPP neurologic monitoring parameters to maintain a desirable cerebral and/or spinal cord blood flow.

Prior use of hypothermia to prevent spinal cord injury has demonstrated clear benefits, but there are methodological drawbacks that limit application of this approach in patients. In the spinal cord, regional spinal cord hypothermia increases spinal cord ischemia tolerance. Hypothermia decreases the extent of CSF glutamate, neurotoxins, and metabolite release and corresponding development of neuronal damage after spinal cord injury. A benefit in patients after selective spinal hypothermia to prevent spinal cord ischemia has also been demonstrated. CSF drainage and avoidance of hypotension are utilized to minimize spinal cord ischemia. It has been shown that subdural and epidural infusion cooling produces localized spinal cord hypothermia concurrently with uniformly distributed pressure increases and can result in spinal cord ischemia. Infusion of a coolant or recirculated cooled CSF into the subdural, epidural or cerebrospinal fluid space increases the spinal fluid volume thereby concurrently increasing the pressure. What is therefore desired is an apparatus and method that combines selective hypothermia with a closed loop catheter without the infusion of coolant into the cerebrospinal fluid or epidural space along with the capability of CSF drainage.

Hypothermia can also alter cerebral vasoreactivity, and may enhance volatile anesthetic-induced vasodilatation of cerebral vessels, which can lead to decreased cerebral blood flow and an increase in ICP. What is desired is a device and methodology that can mitigate this risk and preserve neurologic function in patients requiring anesthesia.

For selective brain and/or spinal cord cooling, in one embodiment of the present disclosure, a flexible heat exchange catheter is inserted into the cerebrospinal fluid space. The catheter has an inflow and outflow lumen for circulation of a coolant by an external coolant and flow regulator. The portion of the catheter in contact with the cerebrospinal fluid can also expand into a balloon but does not necessarily need to expand to transfer heat.

Cerebrospinal fluid is produced by the choroid plexus inside the brain lateral ventricles. The two lateral ventricles communicate with each other through the third ventricle which also opens into the fourth ventricle. The lateral ventricles also communicate with the cerebrospinal fluid in the basal cisterns surrounding the brain stem through the choroidal fissure. The fourth ventricle communicates with the subarachnoid space through the foramen of Magendie and Luschka. The subarachnoid space extends from around the brain, brainstem, and spinal cord. Essentially all of the central nervous system structures and, in particular, the brain and spinal cord, are surrounded by and/or contain cerebrospinal fluid. An apparatus and method that cool the cerebrospinal fluid allow for a faster and more uniform selective central nervous system hypothermia induction and also avoid the systemic toxic side effects of generalized body or blood vessel cooling.

In another embodiment, a catheter has three lumens with two of the lumens communicating at the distal end of the catheter in a closed loop for circulation of the coolant. The third lumen has holes at the distal end of the catheter that allow for drainage of cerebrospinal fluid, as well as intracranial pressure monitoring similar to a ventriculostomy or spinal intrathecal drain. An external coolant and flow regulator controls the coolant temperature and circulation rate, and helps maintain the central nervous system pressure within a desirable range. An external CSF collection chamber also regulates the amount of CSF drainage and helps maintain a desired central nervous system pressure.

The method involves circulating a coolant with a coolant and flow regulator at a controlled temperature and/or flow rate through the closed loop catheter and monitoring the temperature of the central nervous system. To achieve a preprogrammed temperature of the cerebrospinal fluid over a period of time, feedback adjustment of the temperature and/or flow rate of the coolant with an automated control system is undertaken. Feedback adjustment of the cerebrospinal fluid drainage to the measured intrathecal pressure to achieve preprogrammed pressure targets over a period of time with an automated control system is also undertaken.

BRIEF DESCRIPTION OF THE DRAWINGS

FIG. 29 illustrates a treatment flowchart methodology.

DETAILED DESCRIPTION OF THE PREFERRED EMBODIMENTS

Figure 1:
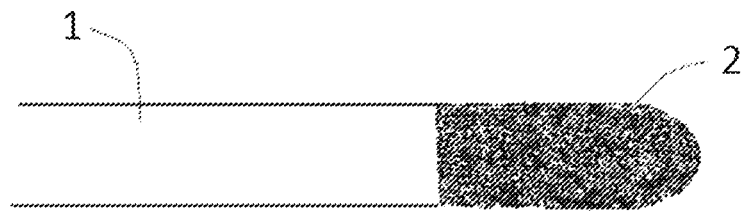
FIG. 1 is a schematic view of a first embodiment of a flexible catheter.
Figure 2:
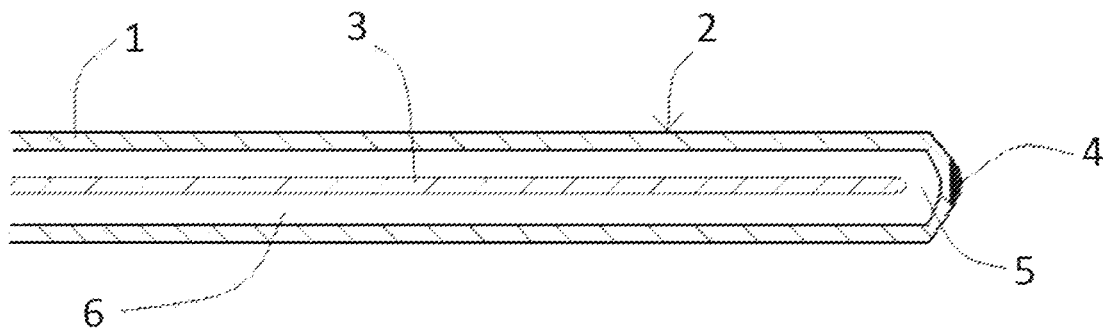
FIG. 2 is a longitudinal cross-sectional view of the first embodiment of the flexible catheter.
Figure 3:
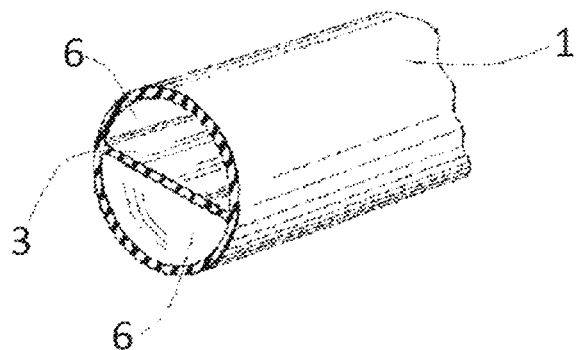
FIG. 3 is a partial sectional view of the first embodiment of the flexible catheter.

In a first embodiment, as shown in FIGS. 1-3, a flexible catheter comprises an outside wall 1 and an inside wall 3. The inside wall 3 divides the lumen of the device into two passages 6 that communicate at a distal end 5 of the catheter. The passages 6 circulate a coolant supplied by a coolant and flow regulator placed external to a patient. The distal end 5 of the catheter is placed inside the desired central nervous system location of the patient. The distal end 5 of the catheter can also include one or more sensors 4 (e.g., pressure, temperature, etc.) that provide information regarding the patient. The distal portion of the catheter can also comprise of a heat conductor 2 to facilitate heat exchange.

Figure 4:
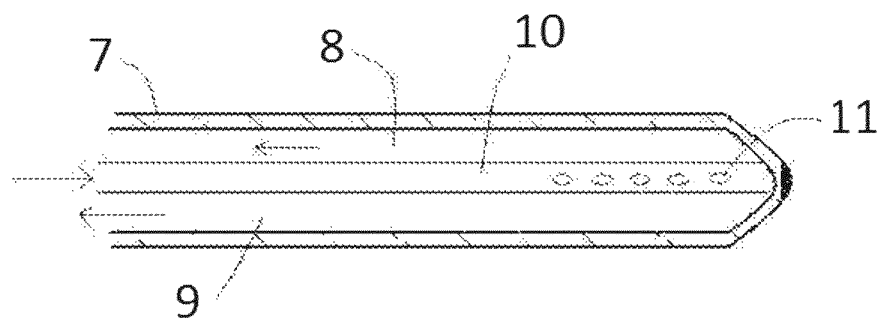
FIG. 4 is a longitudinal cross-sectional view of a second embodiment of a flexible catheter.
Figure 5:
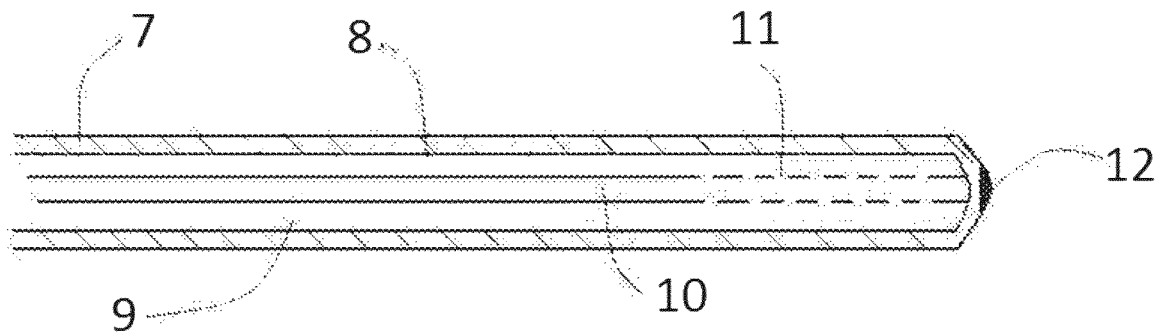
FIG. 5 is a longitudinal cross-sectional view of the second embodiment of the flexible catheter.

In a second embodiment, as shown in FIGS. 4 and 5, a flexible catheter comprises a wall and a central lumen 10 surrounded by two other lumens 8 and 9. The central lumen 10 communicates with the lumens 8 and 9 through holes 11 at the distal end of the catheter and circulates a coolant in the direction illustrated by the arrows in FIG. 4. The catheter can also contain sensors 12 (e.g. pressure, temperature, etc.) at the distal portion that provide information regarding the patient.

Figure 6:
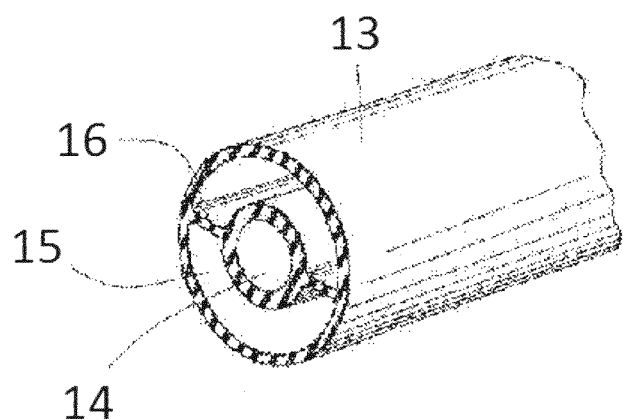
FIG. 6 is a partial sectional view of a third embodiment of a flexible catheter.
Figure 7:
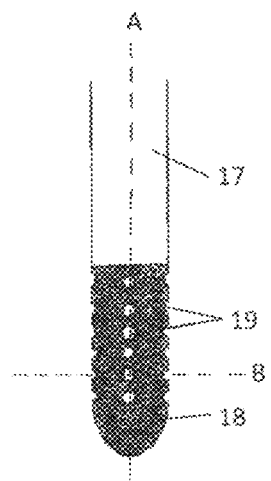
FIG. 7 is a schematic view of a fourth embodiment of a flexible catheter.

In a third embodiment of a flexible catheter, as shown in FIG. 6, a central lumen 14 is surrounded by a lumen 15 with an outer wall 13. A membrane 16 attaches the central lumen 14 to the outer wall 13 and communicates with the surrounding lumen 15 at the distal end of the catheter.

Figure 8:
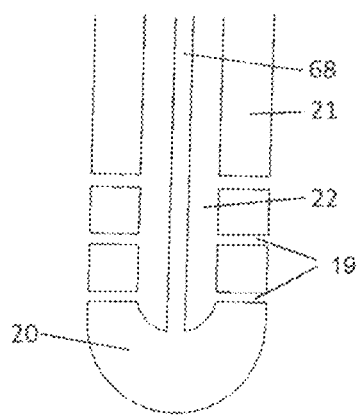
FIG. 8 is a cross-sectional longitudinal view of the fourth embodiment of the flexible catheter taken along line A in FIG. 7.
Figure 9:
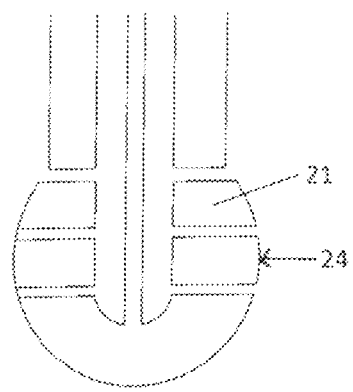
FIG. 9 is a cross-sectional longitudinal view of the fourth embodiment of the flexible catheter taken along line A in FIG. 7 in a dilated state.
Figure 10:
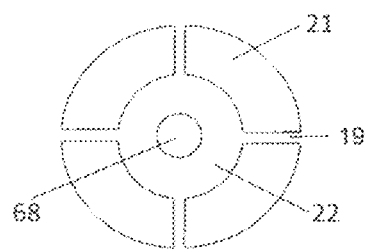
FIG. 10 is a cross-sectional transverse view of the fourth embodiment of the flexible catheter taken along line B in FIG. 7.

In a fourth embodiment, as illustrated in FIGS. 7-10, a flexible catheter has a proximal portion 17 and a distal portion 18. The distal portion 18 has several circumferential holes 19 that allow drainage of cerebrospinal fluid, as well as monitoring of intracranial pressure. As shown in FIGS. 8-10, heat exchange fluid or compressed refrigerant circulates through a central lumen 68 from a distal end 20 of the catheter. The coolant or the gaseous refrigerant enters the distal portion 18 of the catheter through an outer lumen 21, The circulation of the coolant through the catheter cools the distal portion 18, thereby allowing the cerebrospinal fluid surrounding the catheter to be cooled. The catheter includes a lumen 22 that provides for drainage of the cerebrospinal fluid through the circumferential holes 19. The distal portion 18 of the catheter is also capable of expanding like a balloon as illustrated in FIG. 9 when fluid under pressure is circulated through the outer lumen 21.

Figure 11:
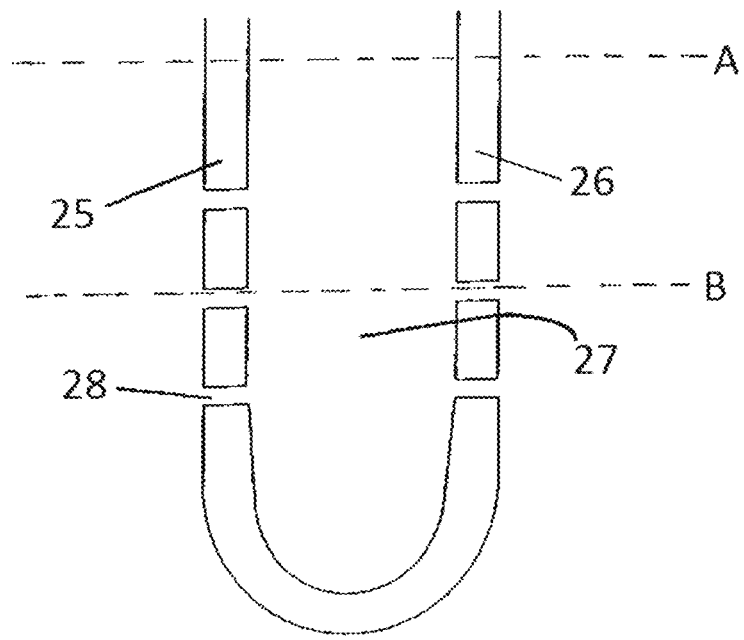
FIG. 11 is a cross-sectional side view of a fifth embodiment of a flexible catheter.
Figure 12:
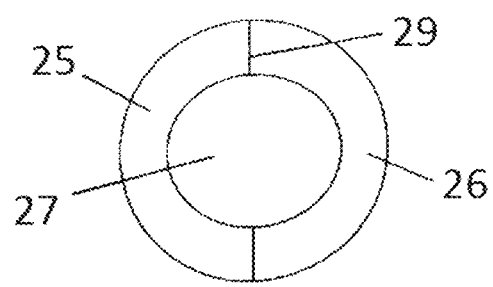
FIG. 12 is a cross-sectional view of the fifth embodiment of the flexible catheter taken along line A in FIG. 11.
Figure 13:
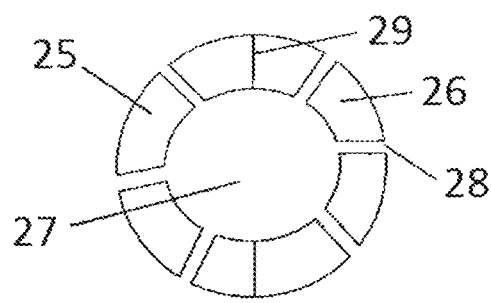
FIG. 13 is a cross-sectional view of the fifth embodiment of the flexible catheter taken along line B in FIG. 11.

In a fifth embodiment of a flexible cooling catheter, as shown in FIGS. 11-13, the catheter includes two lumens 25 and 26. A coolant enters through the lumen 25, flows through a distal end of the catheter and returns through the lumen 26. The lumens 25 and 26 are separated by a membrane 29. The catheter also includes a central lumen 27 that allows drainage of the cerebrospinal fluid through holes 28.

Figure 14:
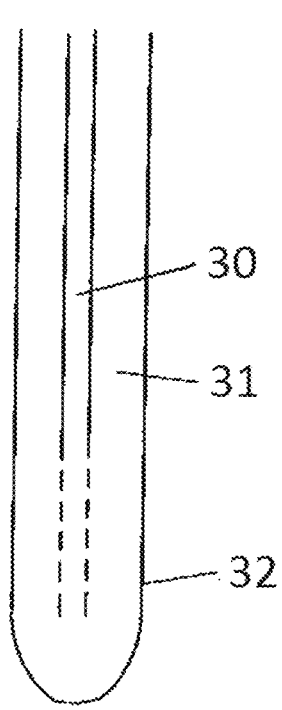
FIG. 14 is a cross-sectional side view of a sixth embodiment of a flexible catheter.
Figure 15:
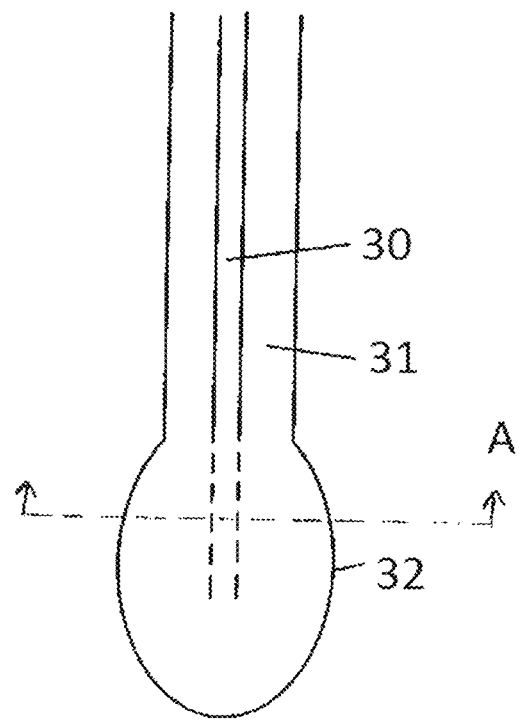
FIG. 15 is another cross-sectional side view of the sixth embodiment of the flexible catheter in FIG. 14.
Figure 16:
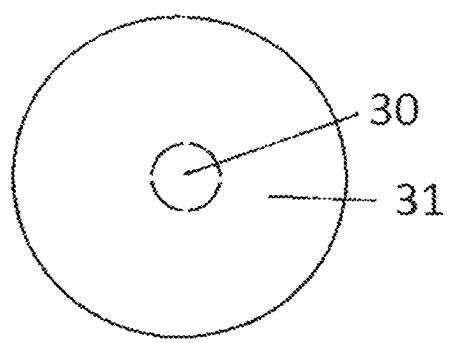
FIG. 16 is a cross-sectional view of the sixth embodiment of the flexible catheter taken along line A in FIG. 15.
Figure 17:
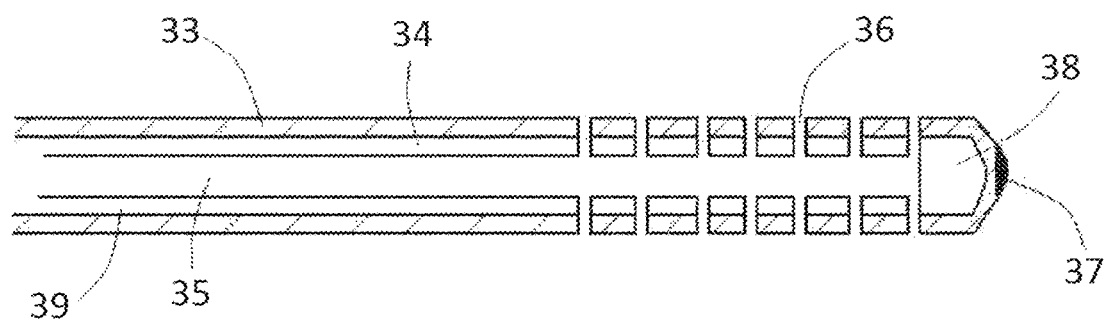
FIG. 17 is a longitudinal cross-sectional view of a seventh embodiment of a flexible catheter.

In a sixth embodiment of a flexible cooling catheter, as shown in FIGS. 14-16, the catheter includes two lumens 30 and 31. A coolant enters into a distal end 32 of the catheter through the lumen 30 and returns from the distal end 32 through the lumen 31. The distal end 32 of the catheter is capable of expanding like a balloon as illustrated in FIG. 15 to increase the surface area that provides heat transfer when the coolant is circulated under pressure.

Figure 18:
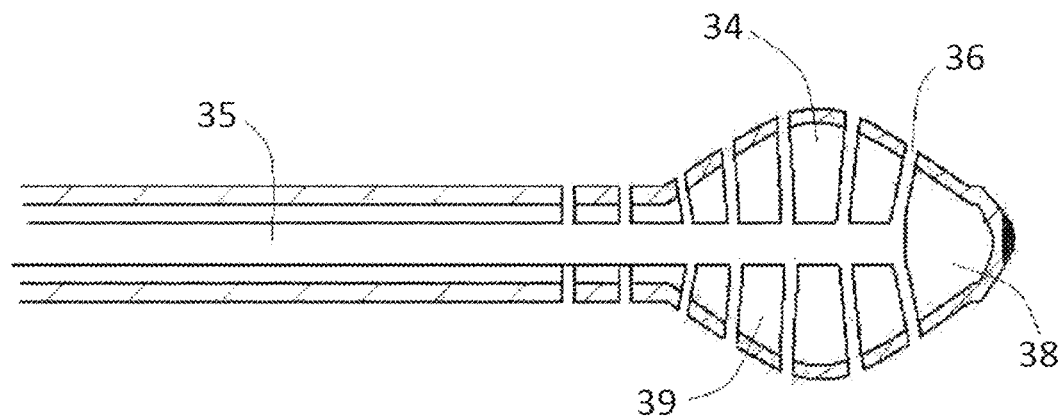
FIG. 18 is a longitudinal cross-sectional view of the seventh embodiment of the flexible catheter with the capability of dilation at its distal portion.
Figure 19:
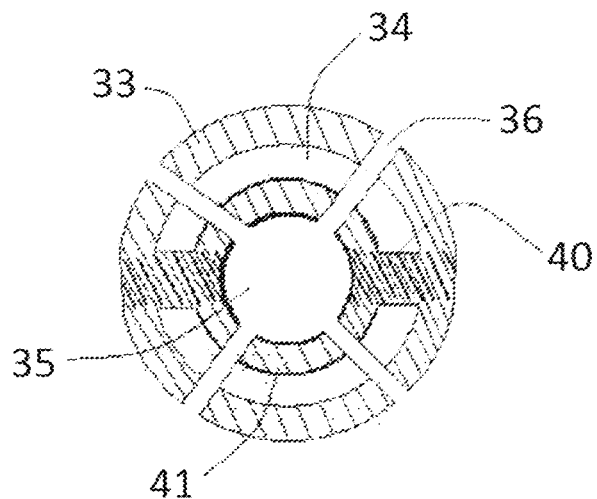
FIG. 19 is a cross-sectional view of the seventh embodiment of the flexible catheter in FIG. 17.
Figure 20:
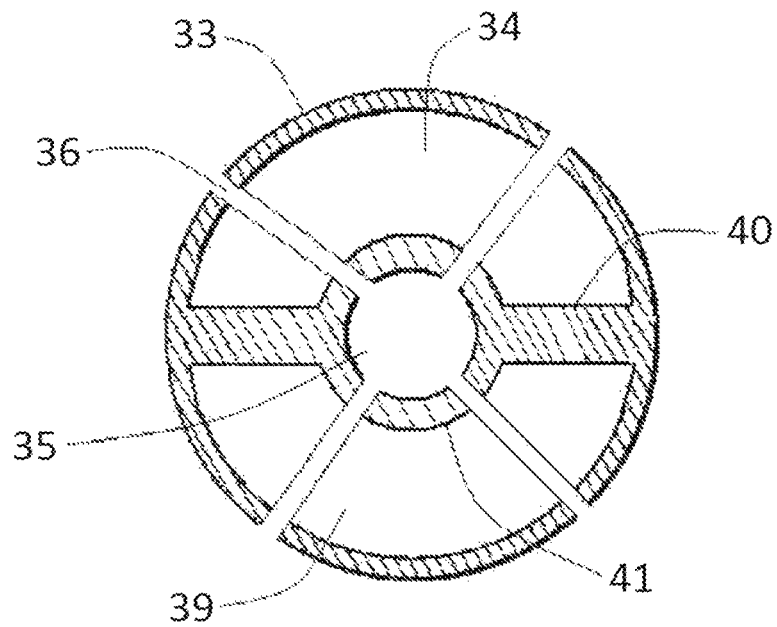
FIG. 20 is a cross-sectional view of the seventh embodiment of the flexible catheter in FIG. 18.

In a seventh embodiment of a flexible catheter, as shown in FIGS. 17-20, the catheter comprises two lumens 34 and 39 and a drainage lumen 35 with ports 36 at a distal end 38 of the catheter. The lumens 34 and 39 are contained between an outer wall 33 and an inner wall 41 of the catheter. The drainage lumen 35 is used for drainage of cerebrospinal fluid and/or hemorrhage through the ports 36. The lumen 35 can also be used to monitor intracranial pressure similar to a ventriculostomy drain. The inner wall 41 is attached to the outer wall 33 with a membrane 40. A coolant is circulated through the lumens 34 and 39 which communicate at the distal end 38 in a closed loop system. A temperature and/or pressure sensor 37 can also be positioned at the tip or any other location on the catheter to monitor central nervous system temperature and/or pressure. The distal portion of the catheter is capable of expanding with the circulation of the coolant under controlled pressure by dilation of the lumens 34 and 39 as shown in FIGS. 18 and 20.

In another embodiment, a flexible catheter can include one or more distal ends each having a balloon. The balloons can be designed such that, when expanded, they conform to the shape of the central nervous system space into which they are placed. The balloon walls are compliant and conform to a shape most amenable to not increasing the intracranial pressure.

Figure 21:
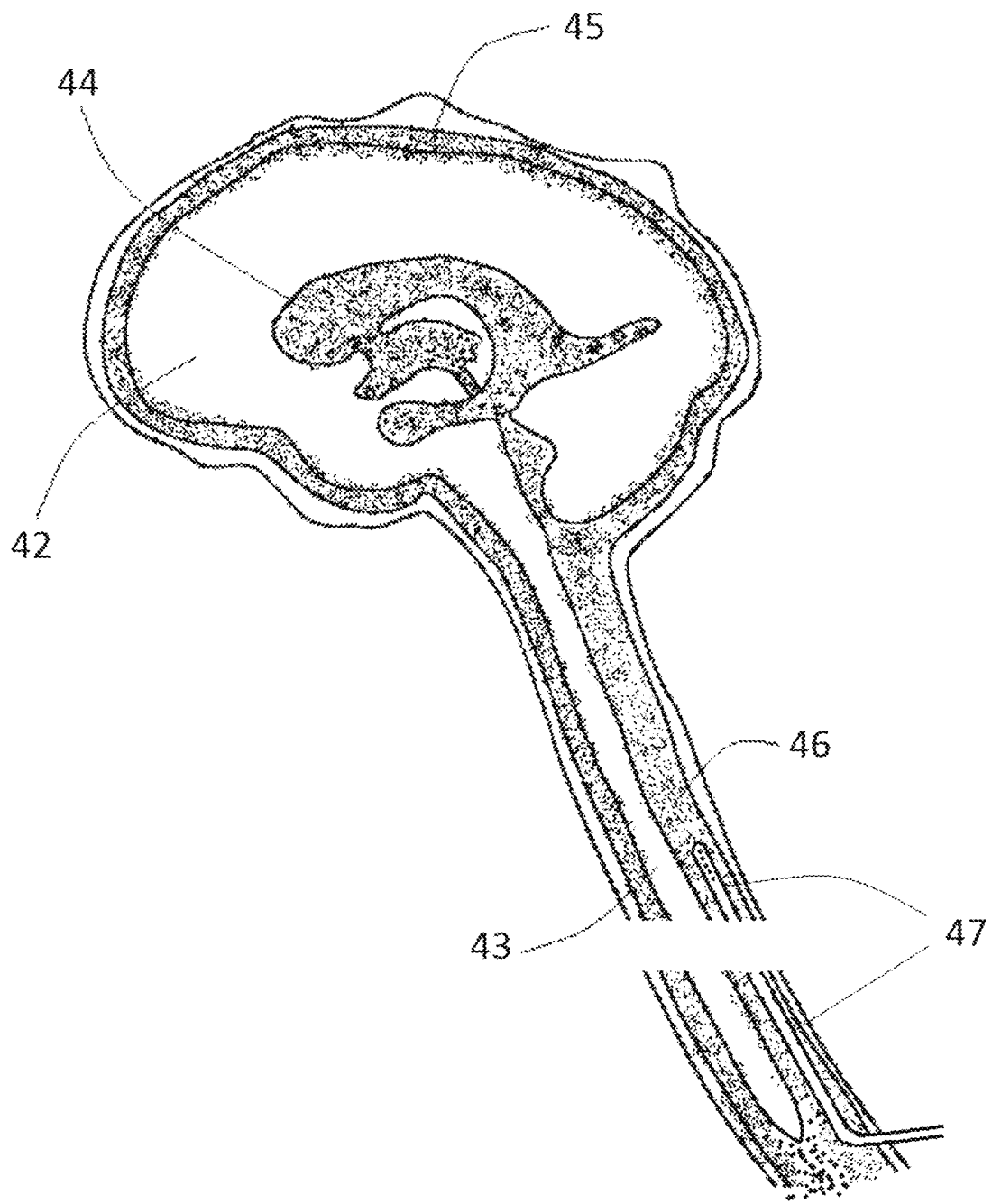
FIG. 21 is a schematic view of the central nervous system and cerebrospinal fluid space with a flexible catheter in the spinal subdural/subarachnoid space.
Figure 22:
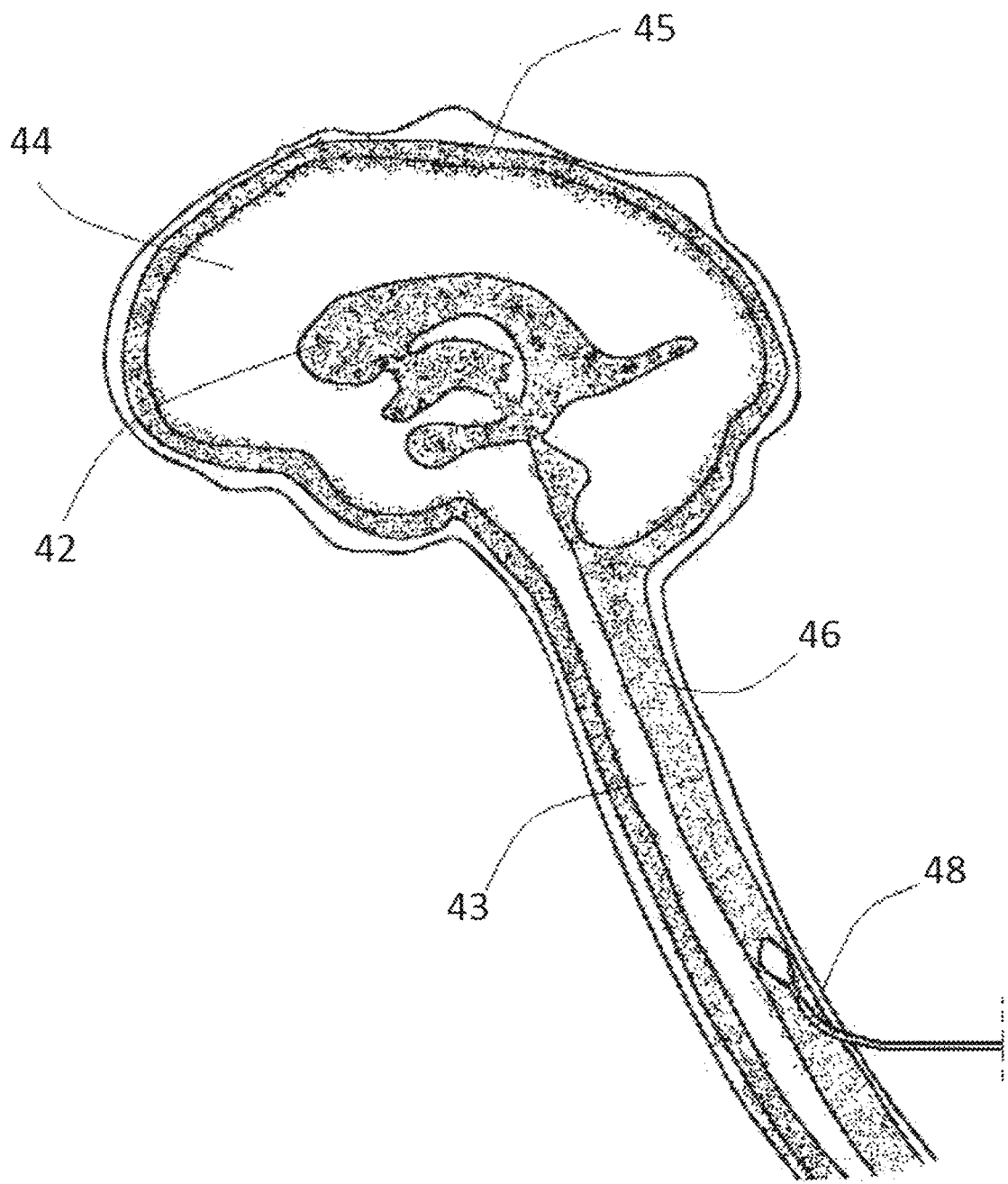
FIG. 22 is a schematic view of a flexible catheter with the distal balloon dilation capability placed in the spinal subdural/subarachnoid space.

As shown in FIGS. 21 and 22, the brain 42 contains cerebrospinal fluid inside the ventricles 44 and is also surrounded by cerebrospinal fluid 45 which is in communication with the cerebrospinal fluid 46 around the spinal cord 43. Cooling of the cerebrospinal fluid provides for selective hypothermia of the brain and spinal cord. Facilitating circulation of the cooled cerebrospinal fluid provides for faster brain and/or spinal cord cooling. The cerebrospinal fluid circulation can be facilitated by a flexible catheter 47 placed in the cerebrospinal fluid 46 without a balloon or a flexible catheter 48 with a balloon. It is also noted that the flexible catheter 47 can be replaced with any embodiment of the flexible catheter described herein that does not expand. Likewise, the flexible catheter 48 can be replaced with any embodiment of the flexible catheter described herein that is capable of expanding.

It is also noted that the flexible catheter 48 with the balloon (or any other flexible catheter described herewith that is capable of expanding) can have its balloon (i.e., expandable portion) dilate and contract in an alternating sequence or a peristaltic format. This sequential dilation and contraction circulates the cerebrospinal fluid inside and outside the brain and/or spinal cord. It is also very prudent that the extent of the device balloon dilation while the device is located inside the central nervous system be controlled so that the ICP is not increased during this process and also to avoid compressive forces on the brain and/or spinal cord. A balloon that conforms to the shape of the space it has been placed inside the central nervous system allows for an increased likelihood of not increasing the ICP with balloon dilation. However, the balloon shape can be round, oval, cylindrical or conform to the shape of the portion of the lateral ventricle in which it is placed to enable a larger surface area for heat exchange, as well as surface contact, but also to avoid excessive compression against the ventricle wall. A highly effective spinal cerebrospinal fluid space location of the device is in the lumbar location, but can also include the cervical or thoracic spine. The device can be placed, for example, post-operatively after a laminectomy, discectomy, or corpectomy. The device can also be placed, for example, through a percutaneous technique similar to the placement of a spinal drain or lumbar puncture. X-ray or fluoroscopy can also be used to locate the correct spinal placement of the device.

Figure 23:
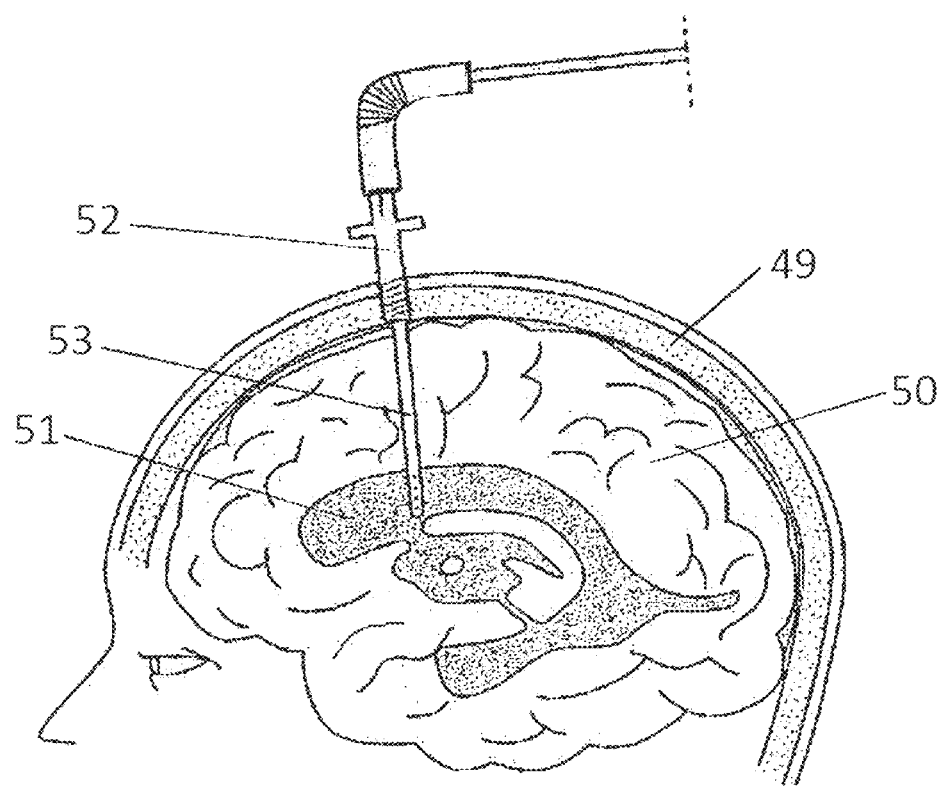
FIG. 23 is a schematic view of a flexible catheter placed in the brain lateral ventricle.

In one method of selective brain and/or spinal cooling, a flexible catheter 53, as shown in FIG. 23, can be placed into a ventricle of the brain 50 or the subdural/intrathecal space of the spine. This allows for cooling of the cerebrospinal fluid and, hence, the brain 50 and/or spinal cord selectively. The catheter 53 can be placed in the lateral ventricles using standard landmarks or can be precisely placed with stereotactic guidance or the use of an endoscope. A bolt 52 can be used to secure the catheter 53 to the skull 49. In this example, the catheter 53 is placed into the cerebrospinal fluid in the ventricle 51. A proximal end of the catheter 53 can be connected to a coolant and flow regulator that controls the circulation of the coolant through the catheter 53, which provides a closed loop cooling system. An automated control system also monitors ICP and temperature through sensors positioned near a distal end of the catheter 53. Further, it is noted that any embodiment of the flexible catheters described herein can be substituted for the flexible catheter 53.

Figure 24:
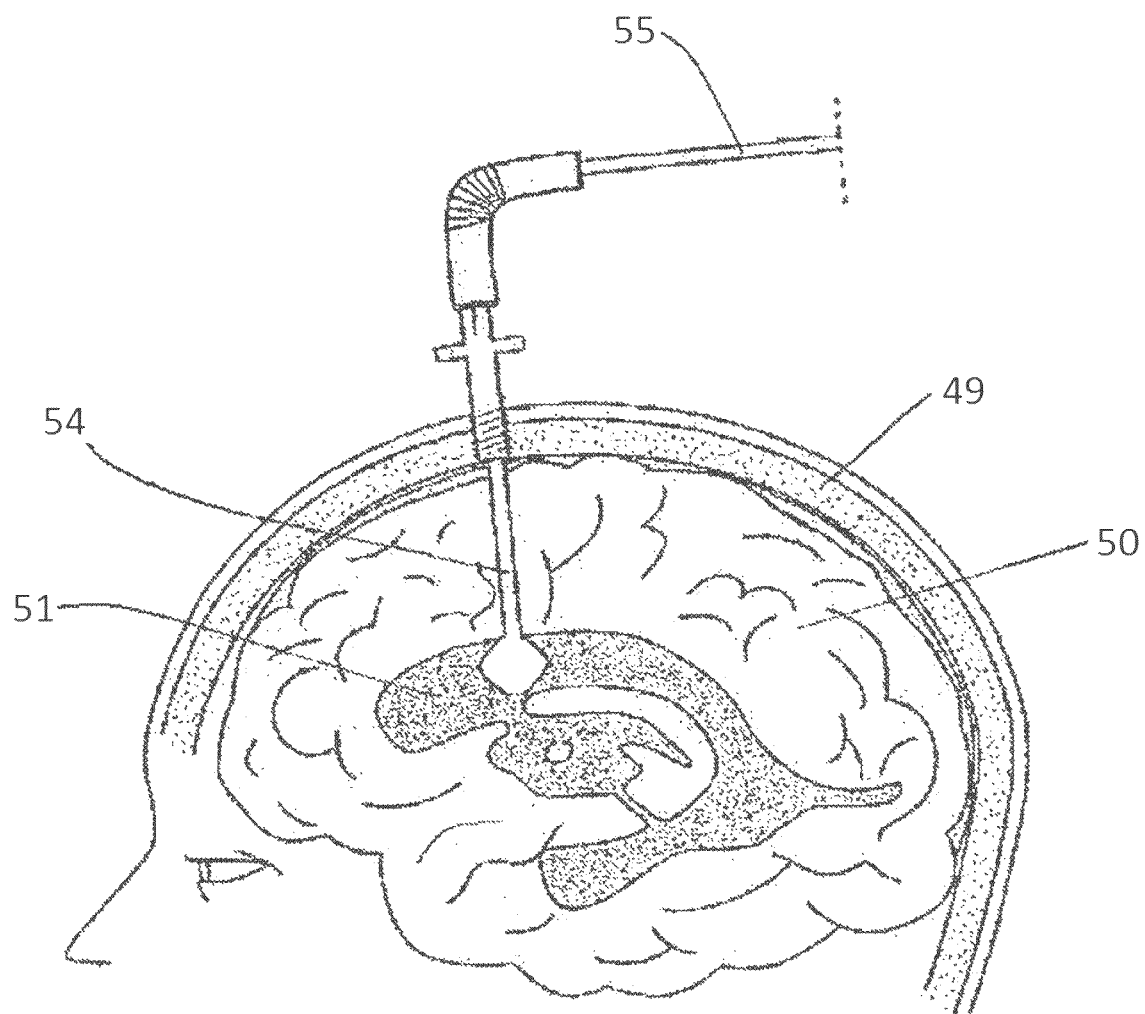
FIG. 24 is a schematically view of a flexible catheter with the distal balloon dilation capability placed in the brain lateral ventricle.

In another method of central nervous system pathology treatment, a flexible catheter 54, as shown in FIG. 24, is placed into a ventricle of the brain 50 or the subarachnoid space of the spine. This allows for cooling of the cerebrospinal fluid and, hence, the brain and/or spinal cord selectively. The effects of the cooling provide for treatment of swelling, traumatic, hypoxic, and ischemic injuries. The catheter 54 can be placed in the lateral ventricles using standard landmarks or can be precisely placed with stereotactic guidance or the use of an endoscope or ultrasound. In this example, the catheter 54 is placed into the cerebrospinal fluid in the ventricle 51 of the brain 50. To place the catheter 54, typically a hole is drilled into the skull 49 to access the brain and the ventricles through a standard ventriculostomy approach. A distal end of the catheter 54 comprises a balloon that is placed in the cerebrospinal fluid. Thus, when the balloon is expanded, creating a greater surface area, heat exchange between the catheter 54 and the cerebrospinal fluid can be increased. A proximal end 55 of the catheter 54 is connected to a coolant and flow regulator that controls the extent of balloon dilation and circulation of the coolant through the catheter 54, which provides a closed loop cooling system. An automated control system can also monitor ICP and temperature through sensors positioned near the balloon end of the catheter 54. Further, it is noted that any embodiment of the flexible catheters described herein that is expandable can be substituted for the flexible catheter 54.

Figure 25:
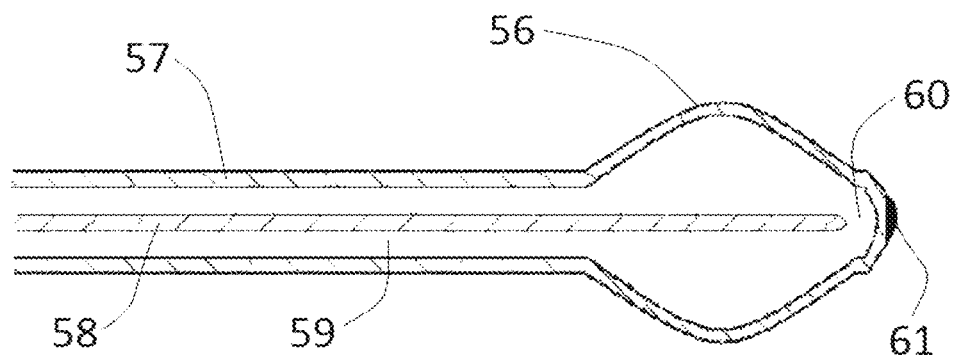
FIG. 25 is a longitudinal cross-sectional view of an eighth embodiment of a flexible catheter.

In an eighth embodiment, as shown in FIG. 25, a flexible catheter comprises an outside wall 57 and an inside wall 58. The inside wall 58 divides a lumen of the catheter into two passages 59 that communicate at a distal end 60 of the catheter. The passages 59 circulate a coolant supplied by a coolant and flow regulator placed external to a patient. The distal end 60 of the catheter is placed inside the desired central nervous system location of the patient. The distal end 60 of the catheter can also include of one or more sensors 61 (e.g., pressure, temperature, etc.) that provide information regarding the patient. The catheter also includes a balloon 56 at the distal end 60. FIG. 25 shows the distal balloon 56 completely dilated. As described above, the pulsating dilation and contraction of the balloon 56 circulates the cerebrospinal fluid outside the balloon and the circulating coolant in the passages 59 cools the cerebrospinal fluid. The increased surface area provided by the balloon expansion allows for a greater degree of heat exchange.

Figure 26:
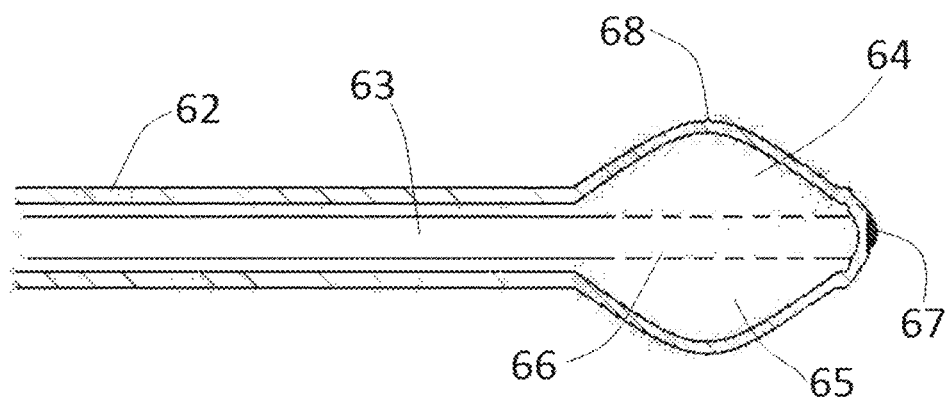
FIG. 26 is a longitudinal cross-sectional view of a ninth embodiment of a flexible catheter.

In a ninth embodiment, as shown in FIG. 26, a flexible catheter comprises a wall 62 and a central lumen 63 surrounded by lumens 64 and 65. The lumen 63 communicates with the lumens 64 and 65 through holes 66 at a distal end of the catheter and circulates a coolant. The catheter also includes a balloon 68 at its distal end. The catheter can also contain sensors 67 (e.g., pressure, temperature, etc.) at the distal portion that provide information regarding the patient. The balloon 68 is completely dilated in FIG. 26. The balloon 68 can also expand and contract in a pulsating format with circulation of the coolant by an external coolant and flow regulator as described above. This pulsating expansion and contraction of the balloon creates a wave in the cerebrospinal fluid where the balloon tip is placed and facilitates circulation of the cooled cerebrospinal fluid throughout the central nervous system.

Figure 27:
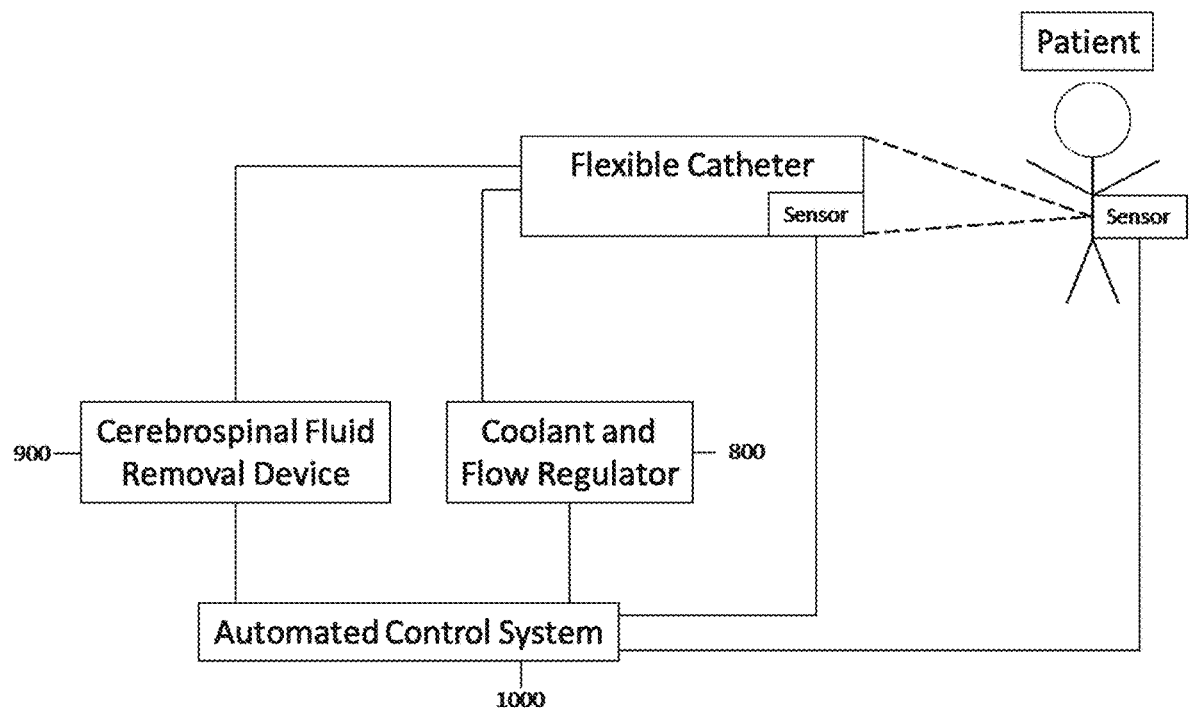
FIG. 27A is an illustration of a system for treating a patient using a flexible catheter.
FIG. 27B is an illustration of an example of a flexible catheter that can be used in the system illustrated in FIG. 27A.

FIG. 27A illustrates a system for treating a patient using a flexible catheter. The system includes a coolant and flow regulator 800 that circulates coolant through the flexible catheter, a cerebrospinal fluid removal device 900 that removes cerebrospinal fluid from a patient via the flexible catheter, and an automated control system 1000 that controls the operation of the coolant and flow regulator 800 and the cerebrospinal fluid removal device 900 based, at least in part, on data recited from one or more sensors located on the flexible catheter and/or the patient.

The coolant and flow regulator 800 can include, for example, a pump, which is able to circulate the coolant through the flexible catheter, and a temperature control system, which is able to change the temperature of the coolant and maintain the temperature of the coolant within a desired range. The pump can be controlled by the automated control system 1000 to adjust the flow rate of the coolant through the flexible catheter. Also, the automated control system 1000 controls the temperature control system such that the temperature of the coolant is maintained within a desired range.

The cerebrospinal fluid removal device 900 can include, for example, a vacuum negative pressure device to facilitate drainage. The automated control system 1000 is able to control the vacuum negative pressure device to change the amount of negative pressure, which adjusts the rate of removal of the cerebrospinal fluid.

However, it is noted that the cerebrospinal fluid removal device 900 does not need to be controlled by the automated control system 1000. Instead of the vacuum negative pressure device, the cerebrospinal fluid removal device 900 can be, for example, a valve that opens at a set pressure, an anti-reflux valve, an automated collection chamber that allows fluid drainage at a set pressure, a drainage bag that allows fluid drainage at a set pressure based on a location of the bag relative to anatomical landmarks, or any combination thereof.

Figure 27B:
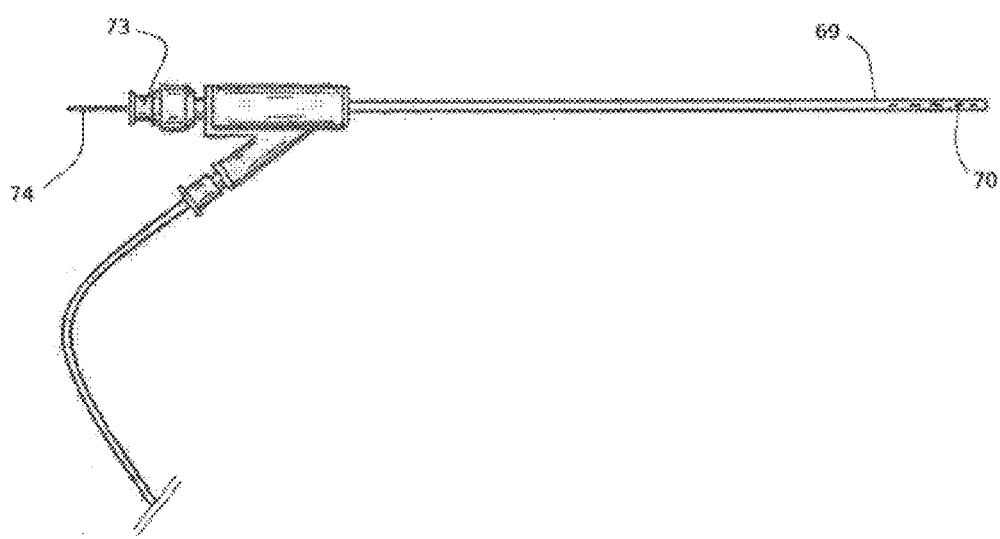

FIG. 27B illustrates a flexible catheter 69 with a distal end comprising drainage ports 70 that can be used with the coolant and flow regulator 800, the cerebrospinal fluid removal device 900, and the automated control system 1000. A proximal portion of the catheter 69 connects to the coolant and flow regulator 800. The catheter also comprises a proximal portion 73 that connects the drain lumen to the cerebrospinal fluid removal device 900. A stylet 74 can also be placed inside the drain lumen of the catheter 69 to assist in the placement of the catheter 69 inside the head or spine. The stylet 74 provides for catheter stiffness to target the exact placement location. The stylet 74 or the catheter 69 can also be registered with markers for camera sensors for navigational purpose. This allows for stereotactic placement of the catheter 69 through image guidance. Alternatively, the catheter 69 can also contain or be embedded with radio-opaque markers to visualize location on x-rays or fluoroscopy. It is also noted that any embodiment of the flexible catheters described herein can be substituted for the flexible catheter 69.

The catheter can be placed in the lateral ventricle of the brain similar to a ventriculostomy drain via, for example, a twist drill hole in the skull, a burr hole or during a craniotomy procedure. The option of a distal balloon increases the surface area to allow faster and more efficient heat exchange and selective cooling by convection to the CSF space, as well as the possibility of direct contact of the ventricle wall lining. An effective spinal cerebrospinal fluid space location of the catheter is in the lumbar location, but can also include the cervical or thoracic spine. Alternatively, the catheter can be placed through the lumbar spine with the distal tip positioned in the thoracic spine. The catheter cools the spinal cord by cooling the CSF, as well as by direct spinal cord surface contact. The catheter can, for example, be placed post-operatively after a laminectomy, discectomy, or corpectomy. The catheter can also be placed through a percutaneous technique similar to placement of a spinal drain or lumbar puncture. X-ray or fluoroscopy can also be used to locate the correct spinal placement of the catheter.

While the above-mentioned various catheter embodiments relate selective hypothermia of the brain and/or spinal cord with the placement of the catheter in the cerebrospinal fluid space along with drainage of the cerebrospinal fluid to treat any increases in intracranial or intrathecal spinal pressure, the current apparatus and method includes monitoring of the neurologic function and adjusting treatment to mitigate any neurologic dysfunction detected by the monitoring.

Various embodiments of the apparatus and method also can include circulating the coolant with, for example, the coolant and flow regulator 800 at a controlled temperature flow rate through the closed loop catheter and monitoring the temperature of the cerebrospinal fluid/central nervous system. To achieve a preprogrammed temperature over a period of time, which could include a few hours to several days, feedback adjustment of the coolant temperature and/or flow rate to the measured cerebrospinal fluid temperature with, for example, the automated control system 1000 is undertaken.

Feedback adjustment of the cerebrospinal fluid drainage to the measured intrathecal pressure to achieve preprogrammed pressure targets over a period of time with the automated control system 1000 controlling, for example, the cerebrospinal fluid removal device 900 is also undertaken. Alternatively, feedback adjustment of the cerebrospinal fluid drainage to maintain a desirable pressure target could be achieved by leveling an external CSF collection bag at a certain height relative to the foramen of Munro which would allow for drainage of CSF until a certain intracranial or intrathecal pressure has been achieved without the need for an automated control system. The height of the CSF collection bag can be based on anatomic landmarks including the ear, external auditory meatus and shoulder providing drainage of CSF at different pressure settings based on the anatomic location.

Muscle MEPs can be used for monitoring motor pathways. Transcranial magnetic or electrical stimulation with a multipulse technique can be used for eliciting MEPs and includes short trains of 5 square-wave stimuli (Single Pulse Duration: 0.5 msec; Interstimulus Interval: 4 msec; and Rate: 2 Hz) through electrodes placed at C1/C2 (lower limbs) and C3/C4 (upper limbs) scalp sites. The MEPs can be, for example, recorded through needle electrodes inserted into the upper- and lower-extremity muscles; they do not require averaging, but they do have wide amplitude and morphological variability. Different warning criteria for MEPs during surgery include, for example, the presence or absence of responses, changes in thresholds, changes in waveform, or amplitude variations. During spinal cord treatment, MEDS should be maintained and preserved; any loss may indicate a complete lower motor neuron lesion, anticipating a motor deficit with little tendency to recover. In case of an alert, physicians should pause the procedure and also consider irrigating with warm saline solution and papaverine while the anesthesiologist increases blood pressure.

SSEPs provide monitoring of the dorsal column and medial lemniscus pathways that carry tactile discrimination, vibration, and joint and/or muscle sensation through, for example, stimulation of the median nerve at the wrist, the posterior tibial nerve at the ankle, and the pudendal nerve (Intensity: 40 mA; Duration: 0.2 msec; and Repetition Rate: 4.3 Hz)) and through recording by electrodes inserted in the scalp at Cz/Fz (legs) and C3/C4/Fz (arms), according to the International 10-20 system of electrode placement. A limitation of SSEPs is that they require averaging, which prolongs their acquisition time. SSE warning criteria are, for example, a 50% drop in amplitude and/or a 10% prolongation in latency. In this scenario, the surgeon should pause the surgical procedure or move toward a different route while continuing the treatment as long as MEPs remain stable.

During surgery involving the spinal cord, it is important to decide where to perform a myelotomy. Anatomic landmarks are often utilized as an indicator for midline intraoperatively. The typical anatomical landmarks for midline of the spinal cord include, for example, the dorsal median sulcus between the dorsal columns and the median dorsal sulcal vein, which enters the midline raphe. A dorsal column mapping technique can be applied to identify the physiological midline. It is helpful for reducing the postoperative morbidity associated with dorsal column dysfunction when an intramedullary cord lesion distorts the normal spinal cord anatomy that results in confusion in distinguishing the midline for the myelotomy. Spinal cord evoked potential (SEP) waves from the dorsal surface of the exposed spinal cord very selectively correlate with the amplitude gradient corresponding to the topographic arrangement of the dorsal column. Because of the somatotopic distribution of ascending fibers in the dorsal column, the highest amplitude close to the midline will usually be recorded after SEP stimulation on the right posterior tibial nerve. By the same reaction from the contralateral side, identification of the physiological midline between these two amplitude peaks can be achieved.

The direct (D) wave spinal tract potential is a direct measure of the number of functioning fast-conducting fibers in the corticospinal tract. As fibers numerically decrease craniocaudally and are absent in the lumbosacral region, the use of D waves is limited in the spinal cord up to T10-11. The D wave is elicited by a single-pulse stimulating technique (0.5 msec duration) and are recorded from the epidural or subdural spaces of the spinal cord. In contrast to MEPs and SSEPs, the D wave is not influenced by blood pressure, heart rate, temperature, and anesthesia drugs, but it needs midline recording. A warning criterion is, for example, a decrease of more than 50% of the baseline amplitude.

Anti D-wave antidromic corticospinal tract potential monitoring can be undertaken, for example, by electrical or magnetic stimulation of the spinal cord with the recordings in scalp (brain cortex) or neck (cervical spinal cord).

Neurogenic MEP is an elicited potential that is electrically stimulated at the spinal cord with epidural or subdural electrodes and then recorded from the peripheral nerves. Neurogenic MEPs are recorded by stimulating the spinal cord through electrodes inserted by a surgical team. A flexible spinal electrode is inserted into the spine proximal to the operating field. The stimulation parameters can be as follows: Intensity: 20-50 mA; Duration of Simulation: 1 ms; and Frequency: 4.1 Hz. Recordings can be performed, for example, at the internal popliteal sciatic nerves or the posterior tibial nerves. This technique allows monitoring of the overall spinal cord. These potentials also contain an antidromical sensory component. The biphasic component corresponds to antidromical activation of the sensory pathways, whereas the polyphasic component corresponds to activation of the motor pathways. Neurogenic MEPs provide combined sensory and motor spinal pathway monitoring Spinal cord evoked potentials (SCEP) are evoked compound potentials from a stimulated spinal cord recorded over the spinal cord. The SCEP correspond to the summation of neural activities originating from the ascending and descending tracts and neurons near the recording electrode. The recorded potentials are very vigorous and represent the combined activity of the tracts of the spinal cord, such as dorsal columns, the corticospinal tracts and others.

Nerve evoked potentials are evoked potentials generated by stimulating a cranial or peripheral nerve and recording activity in the spinal cord or another peripheral nerve. The recordings monitor the nerve and spinal cord functional status.

Monitoring of the spinal cord function with MEP and SSEP provides for a comprehensive monitoring of the spinal cord since the MEP monitors the anterolateral portion of spinal cord involving the corticospinal tract and the SSEPs monitor the posterior portion of the spinal cord and, in particular, the dorsal column. Any functional abnormality in this monitoring usually reflects ischemia from either poor circulation or an increased intrathecal/intracranial pressure. Accordingly, counter measures that can be undertaken would involve, for example, drainage of cerebrospinal fluid with the catheter to decrease the intracranial pressure and increasing the depth of hypothermia with the catheter to mitigate the ischemic effects on the spinal cord, as well as decrease the pressure. Other measures could include, for example, raising the systemic blood pressure with either infusion of intravascular volume, blood transfusion and/or inotropic drugs to improve the cerebral perfusion pressure, as well as a spinal cord perfusion pressure and improve blood flow, re-anastomosing the radicular arteries applying blood flow from the aorta to the spinal cord, especially during aortic aneurysm surgery, decreasing the length of aortic cross-clamping during surgery, and possibly also aborting or temporary halting the surgery until spinal cord function is restored to a normal range. Medications that decrease central nervous system volume and consequently the ICP and/or spinal intrathecal pressure include hyperosmotic agents like mannitol, and hypertonic saline solutions can also be administered if the above measures are not sufficiently effective. Other medications that decrease the metabolic demand of the neurons like barbiturates, pentobarbital, propofol, etc. can also be used to decrease the ICP and/or spinal intrathecal pressure and restore normal neurologic monitoring parameters.

Figure 28:
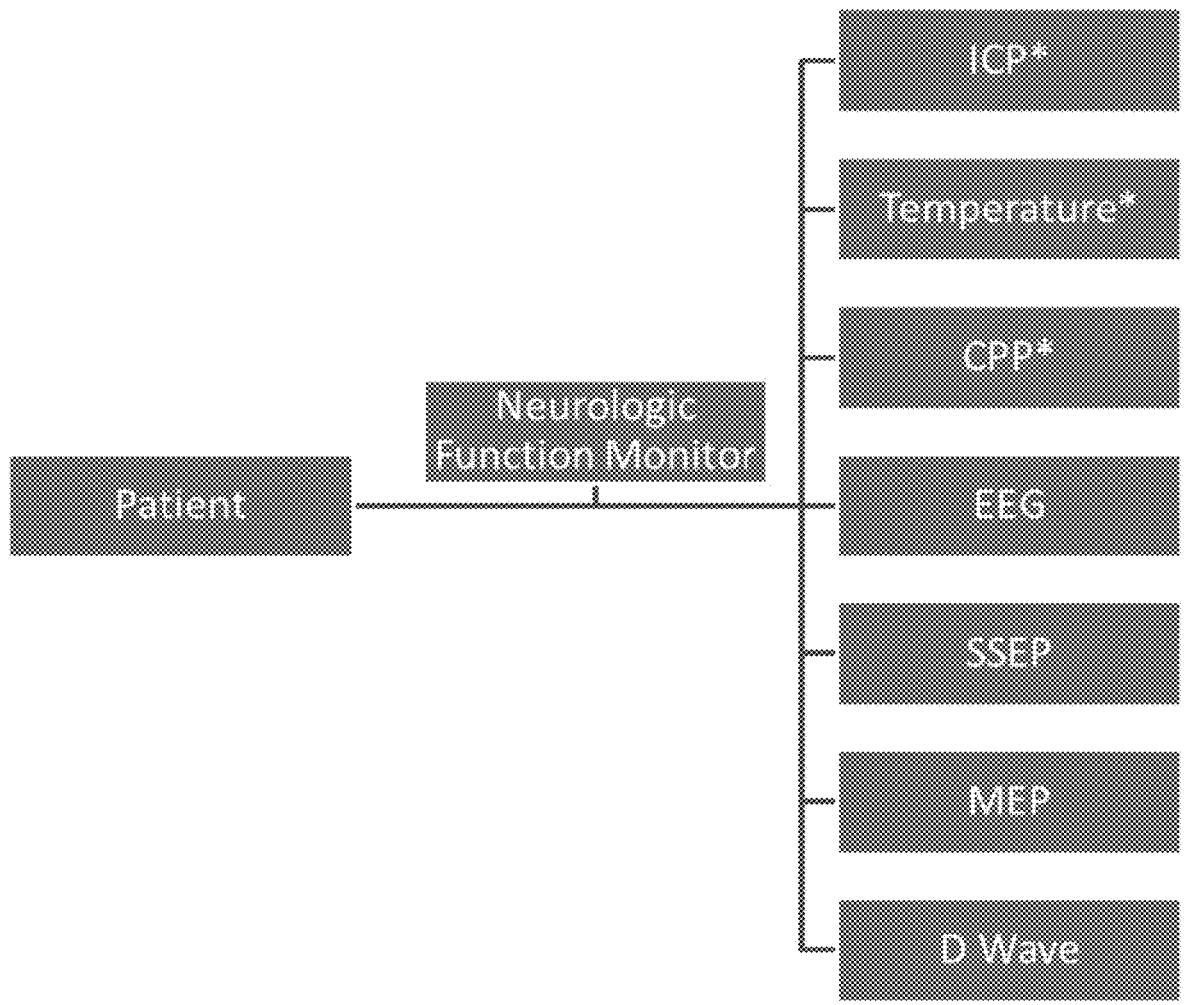
FIG. 28 is a schematic diagram of various neurological monitoring techniques.

FIG. 28 shows a schematic diagram of various neurologic monitoring techniques utilized during surgery and/or in the intensive care unit setting. The intracranial pressure, temperature and/or cerebral perfusion pressure monitoring can be enabled, for example, by the catheter while the EEG, SSEP, EMG, NCS, and/or MEP monitoring can be undertaken, for example, utilizing specific neurologic monitoring equipment. The ICP monitoring can be undertaken, for example, through the catheter drainage lumen connected to an external pressure transducer and/or a pressure probe/sensor at the distal portion of the catheter. The temperature monitoring can be undertaken, for example, by monitoring the temperature of the CSF through the catheter drainage lumen and/or a temperature sensor at the distal portion of the catheter. The CPP (CPP=MAP−ICP) values can be obtained, for example, by the ICP recorded from the catheter, as well as the mean arterial pressure (MAP) from a blood pressure monitor.

In the method, the data from the various neurologic monitoring parameters can also be analyzed by an automated control program which is designed to initiate the appropriate treatment to correct the abnormal monitoring parameter. The SSEP and MEP amplitude and conduction changes can be used to identify spinal cord insult/ischemia. Extreme cooling of the spinal cord can diminish SSEP and MEP signals without any underlying spinal cord abnormality. Similarly, general anesthesia can also diminish SSEP and MEP signals. In order to differentiate diminished SSEP and MEP signals related to spinal cord ischemia/injury from diminished signals related to extreme cooling and/or anesthesia, in one embodiment of the method, monitoring of both the cervical and thoracic spinal cord can be undertaken. Cervical spinal cord monitoring could entail, for example, monitoring the neurologic tracts from the brain to the upper extremities and the thoracic spinal cord monitoring could entail, for example, monitoring the neurologic tracts from the brain to the lower extremities. A decrease in both the cervical and thoracic spinal cord SSEP and/or MEP signals usually implies diffuse spinal cord ischemia/injury which is more likely to be related to anesthesia, extreme hypothermia, or systemic effects. A decrease in thoracic spinal cord SSEP/MEP signals relative to cervical spinal cord SSEP/MEP signals could indicate a thoracic spinal cord ischemia/injury.

FIG. 29 shows a treatment flowchart methodology based on the various abnormal neurologic parameters. An increase in ICP, decrease in CPP, decrease in EEG, decrease in SSEP, and/or a decrease in MEP triggers treatment with an increase in CSF drainage from the catheter until the abnormal neurologic monitoring parameters are corrected. If CSF drainage by the catheter fails to correct the abnormal neurologic monitoring parameter, then central nervous system pressure is further decreased by inducing a deeper selective hypothermia enabled by the catheter by increasing the rate of coolant flow and/or decreasing the circulating coolant temperature further. If these measures also do not correct the abnormal neurologic parameter, then increasing the CPP by raising the MAP can be undertaken. The MAP can be increased by administration of intravenous fluids, blood transfusions, and/or inotropic medications. If the neurologic monitoring parameters continued to remain abnormal, then medications to reduce the ICP including hyperosmolar agents, hypertonic saline, diuretics, and/or metabolism reduction can be used. Hyperosmolar agents include medications like mannitol, urea, etc. Metabolism reduction medications include barbiturates like Versed, Ativan, Valium, etc., as well as propofol and pentobarbital. If none of these measures, either individually or in some combination, correct the abnormal monitoring parameter, then anesthetic and/or surgical maneuvers can be undertaken. Anesthetic maneuvers may include discontinuing or reversing anesthetic medications/agents, which induce vasodilation of the systemic vessels, as well as cerebral vessels, and consequently decrease the CPP. Surgical maneuvers can entail, for example, halting or aborting spinal or aortic surgery, which can also directly impact the neurologic function and monitoring changes particularly in the SSEP and MEP. Re-anastomosis or grafting of the disrupted radicular/intercostal blood vessels supplying blood from the aorta to the spinal cord can also be undertaken. A decompressive craniectomy can also address increased ICP and decreased EEG changes not corrected with the aforementioned treatment maneuvers.

Both SSEP and MEPs are affected by various pharmacological and physiological factors. Any drug or physical parameter that influences electrical conduction along an axon may alter the evoked potential waveform. In general, the longer the synapses tracts are, the more sensitive they are. Furthermore, a greater number of pulses could be needed for lower extremity recordings compared with upper extremity sites because it is usually easier to obtain signals from the upper extremity than from the lower extremity. This is because the hand area occupies a larger representation on the motor cortex. Inhaled anesthetics can reduce the amplitude and increase latency, while intravenous anesthetics can have the same effect, but usually to a lesser degree. Halogenated or nitrous oxide-based agents can influence SSEP amplitude and latency. MEPs are generally more sensitive to anesthetics than SSEPs. Total intravenous anesthesia without neuromuscular blockade is material to muscle MEPs to allow EMG monitoring. Typically, induction with short-acting muscle relaxants, a continuous infusion of propofol and fentanyl and low level nitrous oxide use (not exceeding 50% by volume) are used for MEP monitoring.

For surgery, in one example, anesthesia is maintained with a continuous infusion of propofol (10 mg/kg per hour) and remifentanil (0.25 mg/kg per minute). At induction, a single bolus of non-depolarizing short acting muscle relaxant (rocuronium) is given to facilitate tracheal intubation and ventilation. The level of neuromuscular block is monitored by recording the EMG to a train of 4 stimuli.

Figure 30:
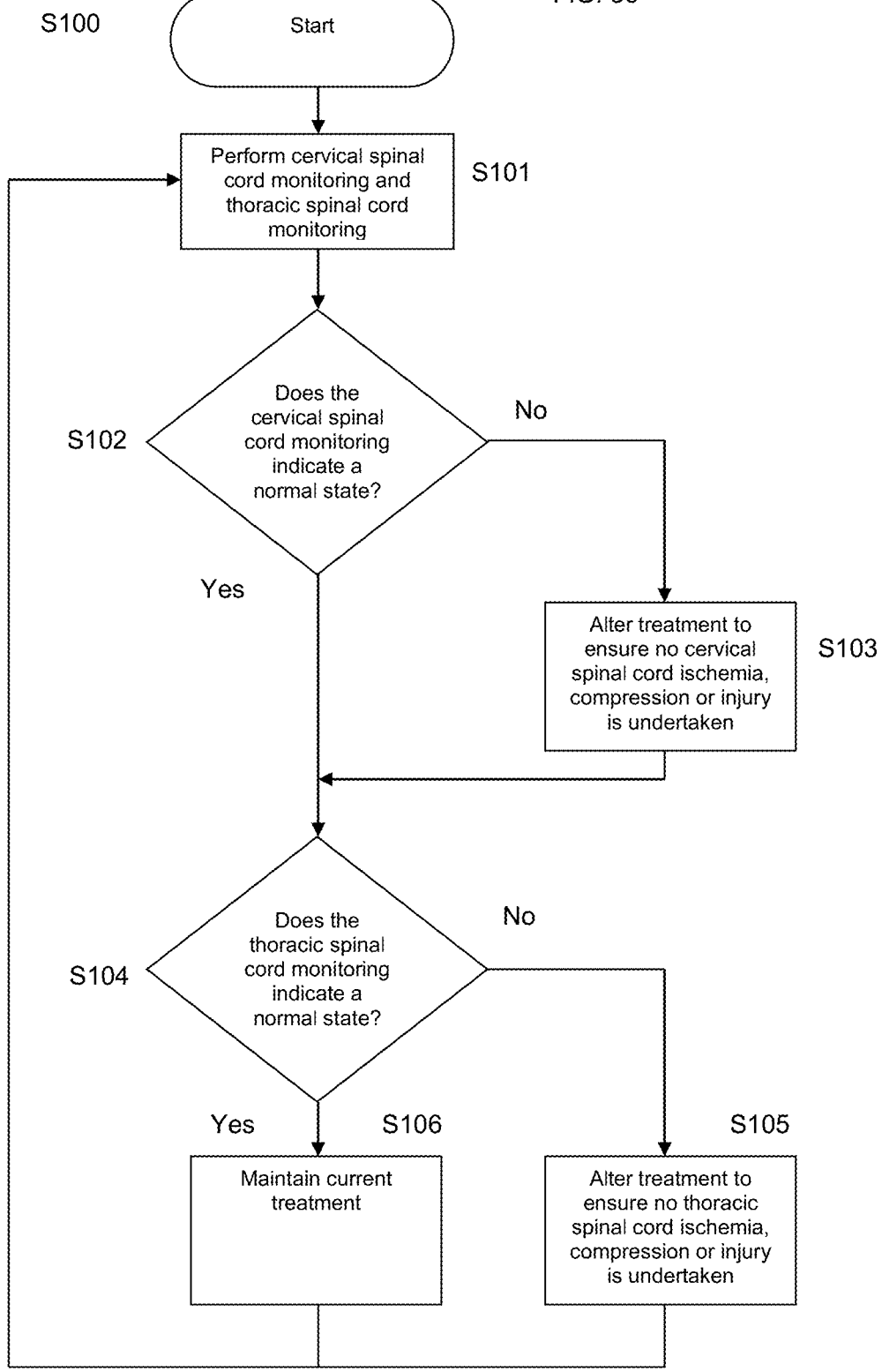
FIG. 30 illustrates a first example of a method for treatment of a brain and/or spinal cord of a patient.

FIG. 30 illustrates an example of the operation of the automated control system 1000 for determining whether the treatment of a patient should be altered. After the automated control system 1000 starts (S100), the automated control system 1000 begins performing cervical spinal cord monitoring and thoracic spinal cord monitoring (S101). The automated control system 1000 then makes a determination as to whether or not the cervical spinal cord monitoring indicates a normal state (S102).

If the cervical spinal cord monitoring does not indicate a normal state (No), the automated control system 1000 alters the treatment to ensure that no cervical spinal cord ischemia, compression or injury is undertaken (S103). Specific examples that could lead to a decrease in cervical spinal cord monitoring would include cervical stenosis exacerbated with movement, positioning, extension or flexion of the neck during intubation, as well as subclavian or vertebral artery decreased flow, dissection, or stenosis impairing blood flow to the cervical spinal cord.

If the cervical spinal cord monitoring does indicate a normal state (Yes), the automated control system 1000 then makes a determination as to whether or not the thoracic spinal cord monitoring indicates a normal state (S104). If the thoracic spinal cord monitoring does not indicate a normal state (No), the automated control system 1000 alters the treatment to ensure no thoracic spinal cord ischemia, compression or injury is undertaken (S105). In this scenario, treatment alteration is focused on conditions that can affect the thoracic spinal cord function and include ischemia related to aortic clamping, aortic dissection or aneurysm, disruption of the intercostal/radicular vessels supplying blood to the spinal cord, and compression of the spinal cord during spinal surgery or manipulation.

If the thoracic spinal cord monitoring indicates a normal state (Yes), the automated control system 1000 maintains the current treatment (S106) and continues the monitoring.

Figure 31:
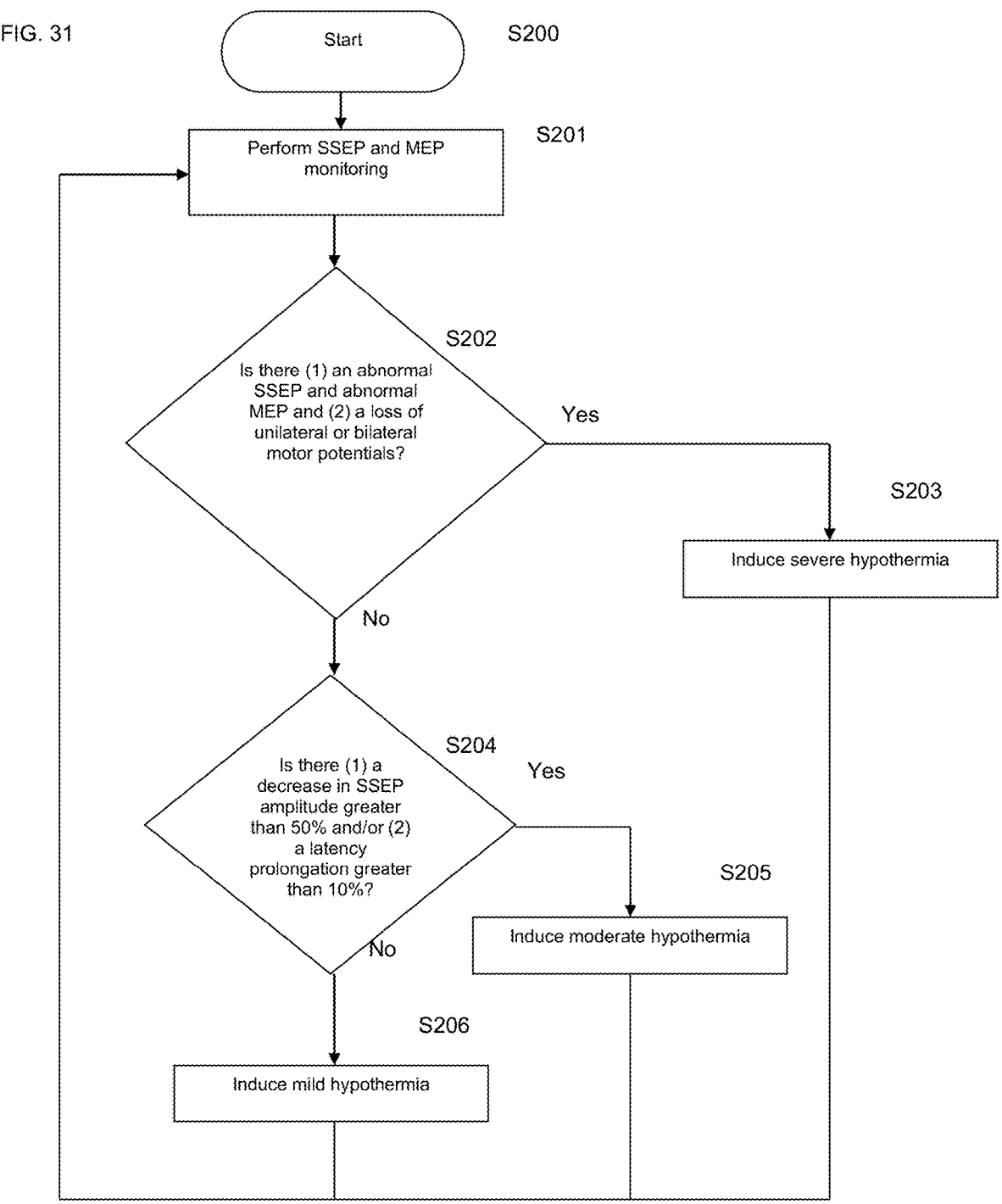
FIG. 31 illustrates a second example of a method for treatment of a brain and/or spinal cord of a patient.

FIG. 31 illustrates an example of the operation of the automated control system 1000 for altering the extent of selective spinal cord hypothermia based on the spinal cord functional monitoring status with SSEP and MEP. After the automated control system 1000 starts (S200), the automated control system 1000 begins monitoring the SSEP and MEP (S201). The automated control system 1000 then makes a determination as to whether or not there is (1) an abnormal SSEP and an abnormal MEP and (2) a loss of unilateral or bilateral motor potentials (S202). If there is (1) an abnormal SSEP and an abnormal MEP and (2) a loss of unilateral or bilateral motor potentials (Yes), the automated control system 1000 induces severe hypothermia (S203) with the CSF/spinal cord temperature maintained at less than 28° C. to protect the spinal cord function and continues to monitor the SSEP and MEP.

If there is not (1) an abnormal SSEP and an abnormal MEP and (2) a loss of unilateral or bilateral motor potentials (No), the automated control system 1000 then makes a determination as to whether or not there is (1) a decrease in SSEP amplitude greater than 50% and/or (2) a latency prolongation greater than 10% (S204).

If there is (1) a decrease in SSEP amplitude greater than 50% and/or (2) a latency prolongation greater than 10% (Yes), the automated control system 1000 induces moderate hypothermia (S205) with the CSF/spinal cord temperature maintained between 28-33° C. to protect the spinal cord function and continues to monitor the SSEP and MEP. If there is not (1) a decrease in SSEP amplitude greater than 50% and/or (2) a latency prolongation greater than 10% (No), the automated control system 1000 induces mild hypothermia (S206) with the CSF/spinal cord temperature maintained between 33-35° C., and continues to monitor the SSEP and MEP.

The automated control system 1000 is able to selectively induce mild, moderate or severe hypothermia by, for example, controlling the coolant and flow regulator 800 to change the temperature of the cooling fluid and/or the flow rate of the cooling fluid supplied to the closed loop within the catheter.

Figure 32:
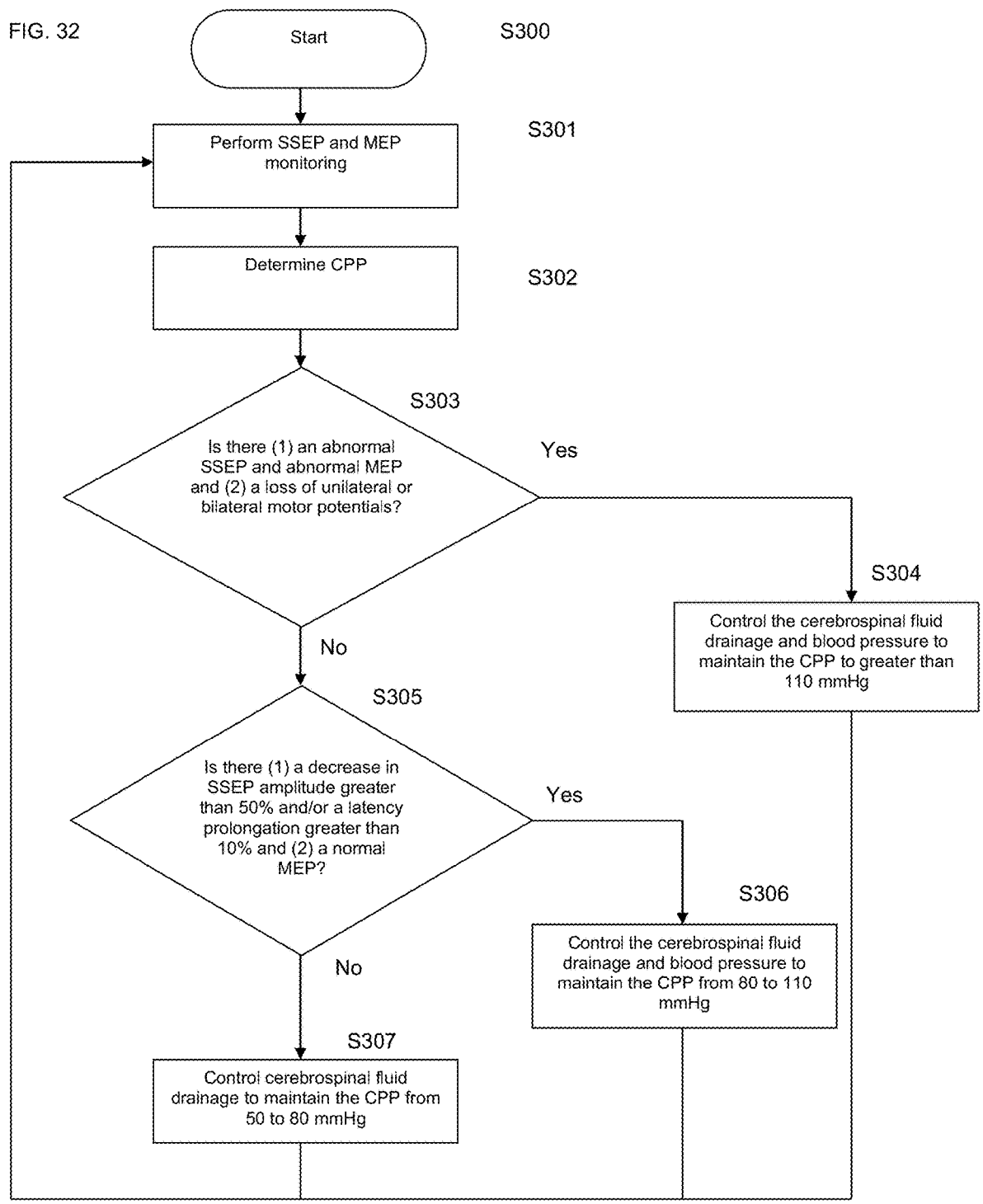
FIG. 32 illustrates a third example of a method for treatment of a brain and/or spinal cord of a patient.

FIG. 32 illustrates an example of the operation of the automated control system 1000 for altering the CPP and extent of cerebrospinal fluid drainage/ICP based on the spinal cord functional monitoring status with SSEP and MEP. The CPP value is obtained from a combination of a mean arterial pressure and intracranial or intraspinal pressure. After the automated control system 1000 starts (S300), the automated control system 1000 begins monitoring the SSEP and MEP (S301). The automated control system 1000 then determines the CPP (S302).

The automated control system 1000 then makes a determination as to whether or not there is (1) an abnormal SSEP and abnormal MEP and (2) a loss of unilateral or bilateral motor potentials (S303). If there is (1) an abnormal SSEP and abnormal MEP and (2) a loss of unilateral or bilateral motor potentials (Yes), the automated control system 1000 controls the cerebrospinal fluid drainage and blood pressure to maintain the CPP to be greater than 110 mmHg (S304) and continues to monitor the SSEP and MEP.

If there is not (1) an abnormal SSEP and abnormal MEP and (2) a loss of unilateral or bilateral motor potentials (No), the automated control system 1000 then makes a determination as to whether or not there is (1) a decrease in SSEP amplitude greater than 50% and/or a latency prolongation greater than 10% and (2) a normal MEP (S305). If there is (1) a decrease in SSEP amplitude greater than 50% and/or a latency prolongation greater than 10% and (2) a normal MEP (Yes), then the automated control system 1000 controls the cerebrospinal fluid drainage and blood pressure to maintain the CPP from 80 to 110 mmHg (S306) and continues to monitor the SSEP and MEP.

If there is not (1) a decrease in SSEP amplitude greater than 50% and/or a latency prolongation greater than 10% and (2) a normal MEP (No), then the automated control system 1000 controls cerebrospinal fluid drainage to maintain the CPP from 50 to 80 mmHg (S307) and continues to monitor the SSEP and MEP. The automated control system 1000 is able to selectively control cerebrospinal fluid drainage, for example, by controlling the cerebrospinal fluid removal device 900 to adjust the amount of cerebrospinal fluid that is removed via the drainage lumen in the catheter.

Figure 33:
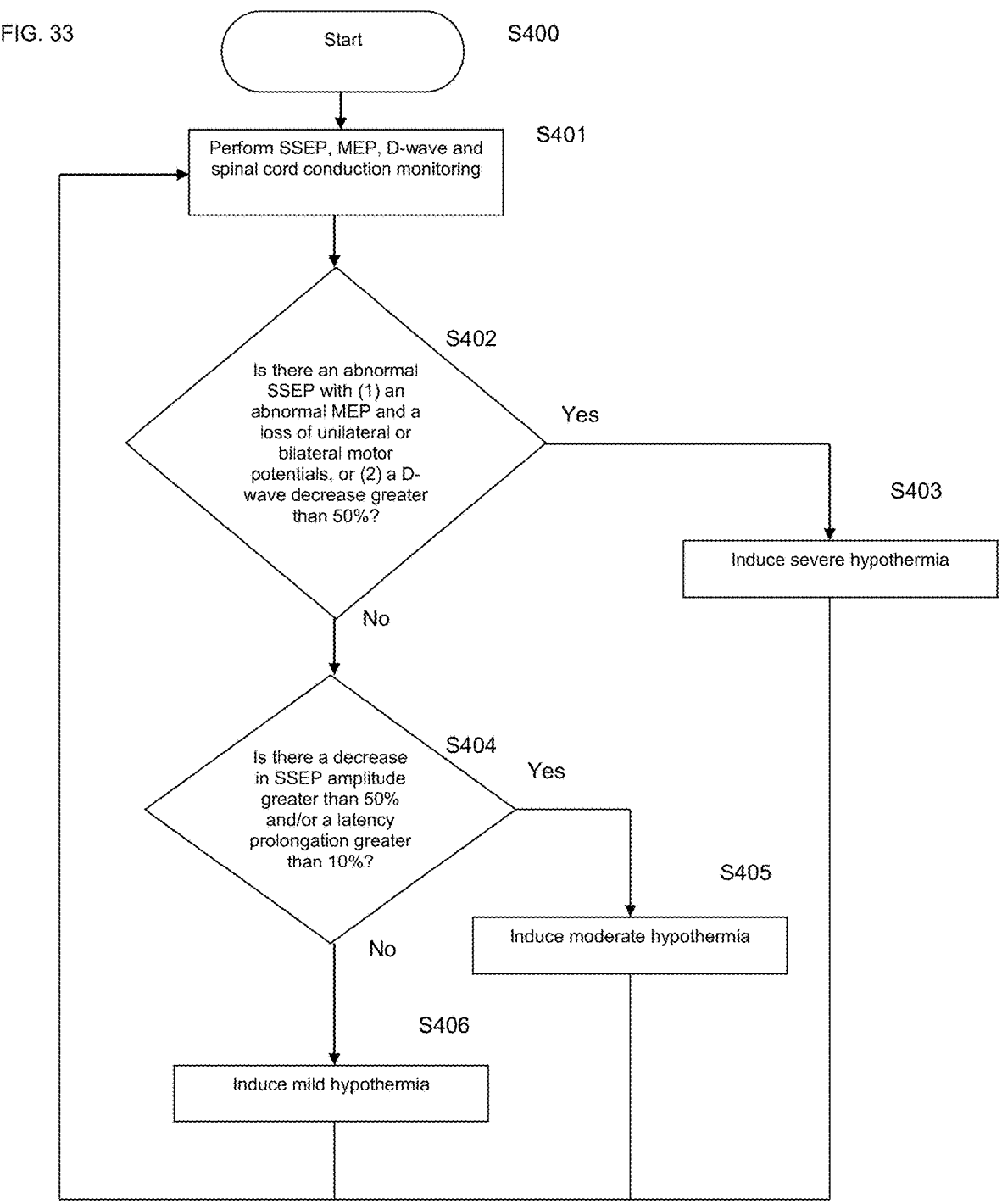
FIG. 33 illustrates a fourth example of a method for treatment of a brain and/or spinal cord of a patient.

FIG. 33 illustrates another example of the operation of the automated control system 1000 for altering the extent of selective spinal cord hypothermia based on the spinal cord functional monitoring status with SSEP, MEP, D-wave, and spinal cord conduction. After the automated control system 1000 starts (S400), the automated control system 1000 begins monitoring the SSEP, MEP, D-wave and spinal cord conduction (S401). The automated control system 1000 then makes a determination as to whether or not there is an abnormal SSEP with (1) an abnormal MEP and a loss of unilateral or bilateral motor potentials, or (2) a D-wave decrease greater than 50% (S402). If there is an abnormal SSEP with (1) an abnormal MEP and a loss of unilateral or bilateral motor potentials, or (2) a D-wave decrease greater than 50% (Yes), the automated control system 1000 induces severe hypothermia (S403) with the CSF/spinal cord temperature maintained at less than 28° C. to protect the spinal cord function and continues to monitor the SSEP, MEP, D-wave and spinal cord conduction.

If there is not an abnormal SSEP with (1) an abnormal MEP and a loss of unilateral or bilateral motor potentials, or (2) a D-wave decrease greater than 50% (No), the automated control system 1000 then makes a determination as to whether or not there is a decrease in SSEP amplitude greater than 50% and/or a latency prolongation greater than 10% (S404).

If there is a decrease in SSEP amplitude greater than 50% and/or a latency prolongation greater than 10% (Yes), the automated control system 1000 induces moderate hypothermia (S405) with the CSF/spinal cord temperature maintained between 28-33° C. to protect the spinal cord function and continues to monitor the SSEP, MEP, D-wave and spinal cord conduction. If there is not a decrease in SSEP amplitude greater than 50% and/or a latency prolongation greater than 10% (No), the automated control system 1000 induces mild hypothermia (S406) with the CSF/spinal cord temperature maintained between 33-35° C., and continues to monitor the SSEP, MEP, D-wave and spinal cord conduction.

The automated control system 1000 is able to selectively induce mild, moderate or severe hypothermia by, for example, controlling the coolant and flow regulator 800 to change the temperature of the cooling fluid and/or the flow rate of the cooling fluid supplied to the closed loop within the catheter.

Figure 34:
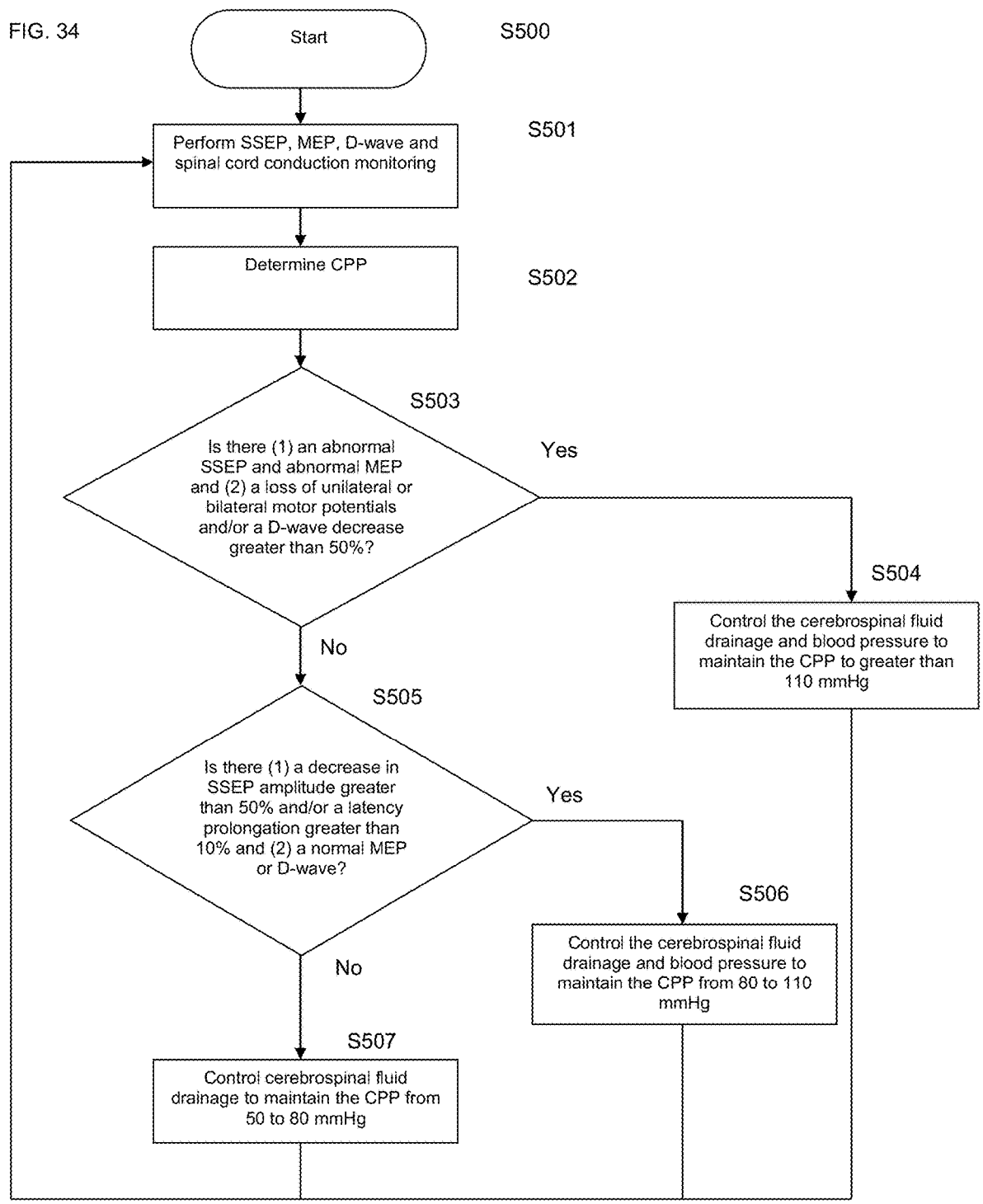
FIG. 34 illustrates a fifth example of a method for treatment of a brain and/or spinal cord of a patient.

FIG. 34 illustrates another example of the operation of the automated control system 1000 for altering the CPP and extent of cerebrospinal fluid drainage/ICP based on the spinal cord functional monitoring status with SSEP, MEP, D-wave, and spinal cord conduction. The CPP value is obtained from a combination of a mean arterial pressure and intracranial or intraspinal pressure. After the automated control system 1000 starts (S500), the automated control system 1000 begins monitoring the SSEP, MEP, D-wave and spinal cord conduction (S501). The automated control system 1000 then determines the CPP (S502).

The automated control system 1000 then makes a determination as to whether or not there is (1) an abnormal SSEP and abnormal MEP and (2) a loss of unilateral or bilateral motor potentials and/or a D-wave decrease greater than 50% (S503). If there is (1) an abnormal SSEP and abnormal MEP and (2) a loss of unilateral or bilateral motor potentials and/or a D-wave decrease greater than 50% (Yes), the automated control system 1000 controls the cerebrospinal fluid drainage and blood pressure to maintain the CPP to be greater than 110 mmHg (S504) and continues to monitor the SSEP, MEP, D-wave and spinal cord conduction.

If there is not (1) an abnormal SSEP and abnormal MEP and (2) a loss of unilateral or bilateral motor potentials and/or a D-wave decrease greater than 50% (No), the automated control system 1000 then makes a determination as to whether or not there is (1) a decrease in SSEP amplitude greater than 50% and/or a latency prolongation greater than 10% and (2) a normal MEP or D-wave (S505). If there is (1) a decrease in SSEP amplitude greater than 50% and/or a latency prolongation greater than 10% and (2) a normal MEP or D-wave (Yes), then the automated control system 1000 controls the cerebrospinal fluid drainage and blood pressure to maintain the CPP from 80 to 110 mmHg (S506) and continues to monitor the SSEP, MEP, D-wave and spinal cord conduction.

If there is not (1) a decrease in SSEP amplitude greater than 50% and/or a latency prolongation greater than 10% and (2) a normal MEP or D-wave (No), then the automated control system 1000 controls cerebrospinal fluid drainage to maintain the CPP from 50 to 80 mmHg (S507) and continues to monitor the SSEP, MEP, D-wave and spinal cord conduction.

The automated control system 1000 is able to selectively control cerebrospinal fluid drainage, for example, by controlling the cerebrospinal fluid removal device 900 to adjust the amount of cerebrospinal fluid that is removed via a drainage lumen in the catheter.

Figure 35:
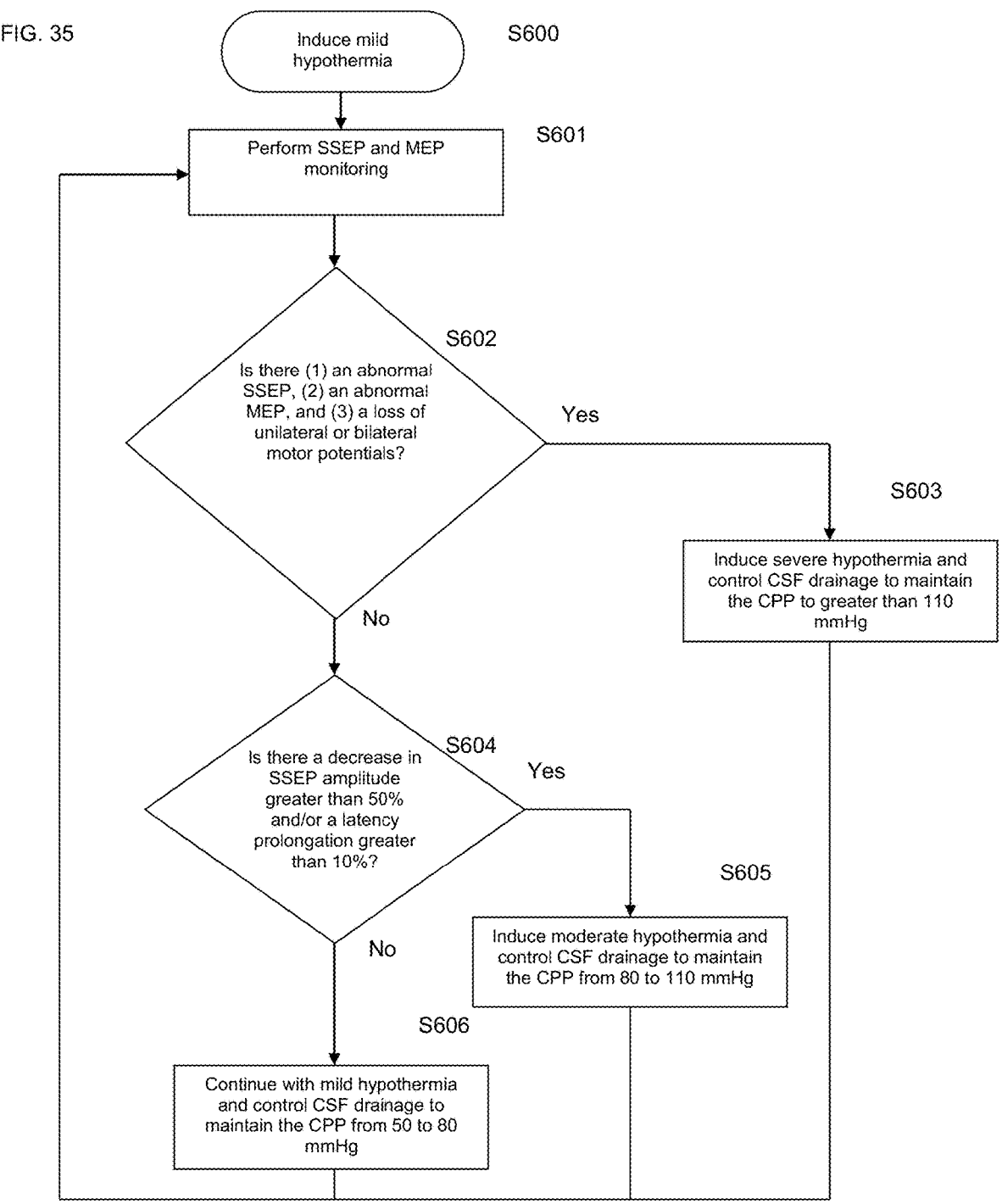
FIG. 35 illustrates a sixth example of a method for treatment of a brain and/or spinal cord of a patient.

FIG. 35 illustrates an example of the operation of the automated control system 1000 for altering the extent of selective spinal cord hypothermia and altering the CPP and extent of cerebrospinal fluid drainage/ICP based on the spinal cord functional monitoring status with SSEP and MEP. After the automated control system 1000 starts by inducing mild hypothermia with the CSF/spinal cord temperature maintained between 33-35° C. (S600), the automated control system 1000 begins monitoring the SSEP and MEP (S601). The automated control system 1000 then makes a determination as to whether or not there is (1) an abnormal SSEP, (2) an abnormal MEP, and (3) a loss of unilateral or bilateral motor potentials (S602). If there is (1) an abnormal SSEP, (2) an abnormal MEP, and (3) a loss of unilateral or bilateral motor potentials (Yes), the automated control system 1000 induces severe hypothermia with the CSF/spinal cord temperature maintained at less than 28° C. to protect the spinal cord function and controls the cerebrospinal fluid drainage to maintain the CPP to be greater than 110 mmHg (S603), and continues to monitor the SSEP and MEP.

If there is not (1) an abnormal SSEP, (2) an abnormal MEP, and (3) a loss of unilateral or bilateral motor potentials (No), the automated control system 1000 then makes a determination as to whether or not there is a decrease in SSEP amplitude greater than 50% and/or a latency prolongation greater than 10% (S604).

If there is a decrease in SSEP amplitude greater than 50% and/or a latency prolongation greater than 10% (Yes), the automated control system 1000 induces moderate hypothermia with the CSF/spinal cord temperature maintained between 28-33° C. to protect the spinal cord function and controls the cerebrospinal fluid drainage to maintain the CPP from 80 to 110 mmHg (S605), and continues to monitor the SSEP and MEP. If there is not a decrease in SSEP amplitude greater than 50% and/or a latency prolongation greater than 10% (No), the automated control system 1000 continues with mild hypothermia with the CSF/spinal cord temperature maintained between 33-35° C. and controls cerebrospinal fluid drainage to maintain the CPP from 50 to 80 mmHg (S606), and continues to monitor the SSEP and MEP.

The automated control system 1000 is able to selectively induce mild, moderate or severe hypothermia by, for example, controlling the coolant and flow regulator 800 to change the temperature of the cooling fluid and/or the flow rate of the cooling fluid supplied to the closed loop within the catheter. Further, the automated control system 1000 is able to selectively control cerebrospinal fluid drainage, for example, by controlling the cerebrospinal fluid removal device 900 to adjust the amount of cerebrospinal fluid that is removed via the drainage lumen in the catheter.

Figure 36:
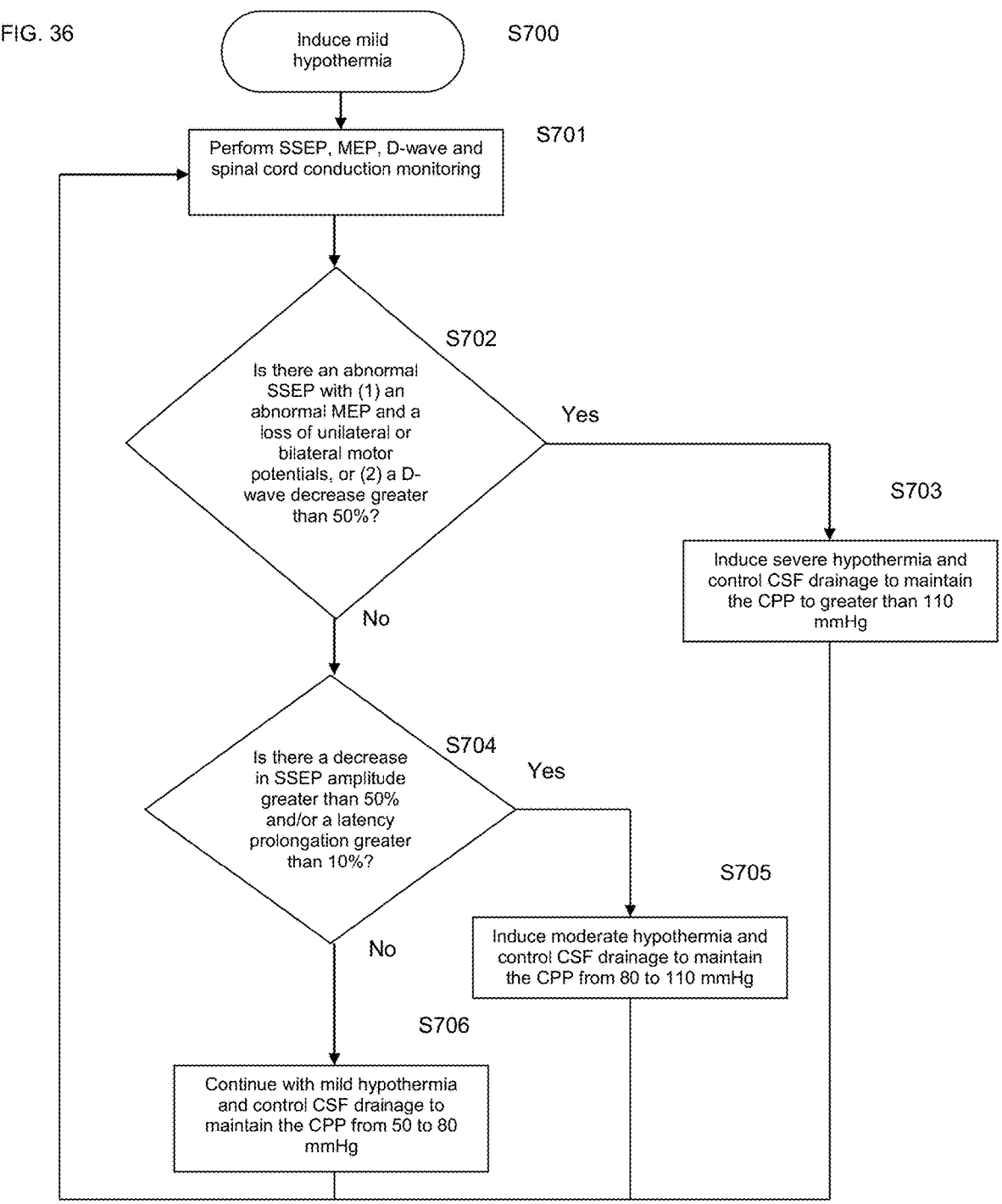
FIG. 36 illustrates a seventh example of a method for treatment of a brain and/or spinal cord of a patient.

FIG. 36 illustrates another example of the operation of the automated control system 1000 for altering the extent of selective spinal cord hypothermia and altering the CPP and extent of cerebrospinal fluid drainage/ICP based on the spinal cord functional monitoring status with SSEP, MEP, D-wave, and spinal cord conduction. After the automated control system 1000 starts by inducing mild hypothermia with the CSF/spinal cord temperature maintained between 33-35° C. (S700), the automated control system 1000 begins monitoring the SSEP, MEP, D-wave and spinal cord conduction (S701). The automated control system 1000 then makes a determination as to whether or not there is an abnormal SSEP with (1) an abnormal MEP and a loss of unilateral or bilateral motor potentials, or (2) a D-wave decrease greater than 50% (S702). If there is an abnormal SSEP with (1) an abnormal MEP and a loss of unilateral or bilateral motor potentials, or (2) a D-wave decrease greater than 50% (Yes), the automated control system 1000 induces severe hypothermia with the CSF/spinal cord temperature maintained at less than 28° C. to protect the spinal cord function and controls the cerebrospinal fluid drainage to maintain the CPP to be greater than 110 mmHg (S703), and continues to monitor the SSEP, MEP, D-wave and spinal cord conduction.

If there is not an abnormal SSEP with (1) an abnormal MEP and a loss of unilateral or bilateral motor potentials, or (2) a D-wave decrease greater than 50% (No), the automated control system 1000 then makes a determination as to whether or not there is a decrease in SSEP amplitude greater than 50% and/or a latency prolongation greater than 10% (S704).

If there is a decrease in SSEP amplitude greater than 50% and/or a latency prolongation greater than 10% (Yes), the automated control system 1000 induces moderate hypothermia with the CSF/spinal cord temperature maintained between 28-33° C. to protect the spinal cord function and controls the cerebrospinal fluid drainage to maintain the CPP from 80 to 110 mmHg (S705), and continues to monitor the SSEP, MEP, D-wave and spinal cord conduction. If there is not a decrease in SSEP amplitude greater than 50% and/or a latency prolongation greater than 10% (No), the automated control system 1000 continues with mild hypothermia with the CSF/spinal cord temperature maintained between 33-35° C. and controls cerebrospinal fluid drainage to maintain the CPP from 50 to 80 mmHg (S706), and continues to monitor the SSEP, MEP, D-wave and spinal cord conduction.

The automated control system 1000 is able to selectively induce mild, moderate or severe hypothermia by, for example, controlling the coolant and flow regulator 800 to change the temperature of the cooling fluid and/or the flow rate of the cooling fluid supplied to the closed loop within the catheter. Further, the automated control system 1000 is able to selectively control cerebrospinal fluid drainage, for example, by controlling the cerebrospinal fluid removal device 900 to adjust the amount of cerebrospinal fluid that is removed via the drainage lumen in the catheter.

While specific numbers are illustrated in these treatment methodologies, it is understood that these number ranges in the selective category can be increased or decreased keeping within the scope of the disclosed methodology.

The embodiments of the method and catheter used in performing the method described herein provide for treatment of any central nervous system pathology including, but not limited to, treatment of increased intracranial pressure, brain swelling or edema, spinal cord edema, trauma, brain injury, skull fracture, stroke, ischemia, hypoxia following respiratory or cardiac arrest, tumors, hemorrhage, infection, seizure, spinal cord injury, spine fractures, arteriovenous malformations, aneurysms, aortic artery surgery related spinal cord ischemia protection, spinal stenosis, herniated disc, cranial surgery, spine surgery, and scoliosis surgery.

The catheter can be placed intracranially following the drilling of a hole in the skull, for example, via a twist drill, burr hole placement, or craniotomy/craniectomy. It can be placed inside the spinal canal in the epidural, subdural or subarachnoid space through, for example, a percutaneous technique or following a laminotomy/laminectomy. Placement of the catheter intracranially or intraspinally can be further facilitated by radiographic guidance (fluoroscopy), ventriculograms, cisternograms, ultrasound, frame based or frameless stereotactic navigation systems, or endoscopy.

The catheter can also comprise radio-opaque markers or be impregnated with barium to visualize correct placement in the central nervous system with x-rays. Highly effective locations for the catheter are, for example, in the cerebrospinal fluid space in the lateral ventricle, subarachnoid space of the brain surface, and adjacent to the thoracic spinal cord with entry through the lumbar intra-thecal space. Other locations, for example, include in the surgical resection bed following a craniotomy for removal of a brain tumor or hemorrhage, and a spinal epidural or intrathecal space following a laminectomy. The catheter can also be secured to the skull, for example, by a hollow bolt. The closed loop cooling system selectively cools the central nervous system without serious side-effects of generalized body cooling and, in some embodiments, also provides for the drainage of fluid (e.g., cerebrospinal fluid or hemorrhage).

Sensors can also be placed at the distal portion of the catheter, which is positioned inside the central nervous system. These sensors can be placed at one location or at multiple locations on the catheter wall. In some embodiments, the sensors monitor pressure and temperature. In other embodiments, water sensors can also be included at positions to detect the cerebrospinal fluid location, for example, inside the ventricle to confirm the correct catheter location, since cerebrospinal fluid predominantly comprises of water. Similarly, impedance sensors can also be included to confirm the location of the catheter as impedance changes from brain to a cerebrospinal fluid location as the catheter is advanced into the lateral ventricle during placement. Other sensors that can be included one the catheter include, for example, cerebrospinal fluid marker sensors, osmolarity sensors, oxygenation sensors, carbonation sensors, metabolite sensors, and/or pH sensors.

The catheter with the capability of cooling and circulation of the cerebrospinal fluid provides for selective cooling of the brain and spinal cord. Since the cerebrospinal fluid is in communication from inside the brain to the outer surface of the brain and spinal cord, placement of the catheter intracranially not only cools the brain, but also the spinal cord. Similarly, cooling of the brain can also be achieved by placement of the catheter inside the spinal canal. Alternatively, at least one catheter can be placed intracranially and at least one other catheter can be placed in the spinal canal to increase the extent of selective central nervous system cooling.

While the embodiments of the catheter and the method for using the catheter described herein along with the illustrations are specific, it is understood that the embodiments are not limited to those disclosed. Numerous modifications, rearrangements, and substitutions to the embodiments can be made with those skilled in the art without departing from the spirit of the embodiments as set forth and defined herein. For example, features of different embodiments can be combined.

The automated control system 1000 can be implemented not only as an apparatus or apparatuses, but also as a method including the steps as discussed above and illustrated in the figures, which methods as discussed above constitute examples of algorithms. The automated control system 1000 can also be implemented as a program on a non-transitory computer-readable medium for causing a computer or processor to execute such steps. The non-transitory computer-readable recording medium could be, for example, a CD-ROM, DVD, Bluray disc, or an electronic memory device. Further, it is noted that one or more of the above-described operations of the method can be performed by a physician or other personnel monitoring and responding to the monitoring changes and informing the surgeon/physician to respond and make the appropriate changes.

The automated control system 1000 may be implemented as any combination of a system, a method, an integrated circuit, and a computer program on a non-transitory computer readable recording medium.

The automated control system 1000 may be formed in multiple chips or formed in one chip. The technology of implementation of the circuitry can be Large Scale Integration (LSI), but may also be an integrated circuit IC, a system LSI, a super LSI, or ultra LSI. These technologies allow for the circuitry of the automated control system 1000 to be integrated as a computer system configured by including a microprocessor, a memory or memories, such as a ROM, a RAM, and the like, wherein a computer program is stored in the memory and the microprocessor implements the stored program to achieve the function of the program.

A method for implementing the integrated circuit is not limited to LSI. The integrated circuit may also be implemented by a dedicated circuit or a versatile processor. If a new technique for integrated circuit production arises, such new technique may be used to implement the blocks shown in the figures.

Components of the apparatus may also be implemented as a specifically programmed general purpose processor, CPU, a specialized microprocessor such as Digital Signal Processor that can be directed by program instructions, a Field Programmable Gate Array (FPGA) that can be programmed after manufacturing, or a reconfigurable processor. Some or all of the functions may be implemented by such a processor while some or all of the functions may be implemented by circuitry in any of the forms discussed above.

The automated control system 1000 may be a non-transitory computer-readable recording medium having recorded thereon a program embodying the methods/algorithms discussed above for instructing a processor to perform the methods/algorithms.

Each of the elements of the automated control system 1000 may be configured by implementing dedicated hardware or a software program controlling a processor to perform the functions of any of the components or combinations thereof. Any of the components may be implemented as a CPU or other processor reading and executing a software program from a recording medium such as a hard disk or a semiconductor memory.

The sequence of the steps included in the above described algorithms and that illustrated in the figures are illustrative, and algorithms having a sequence other than the above described sequences are contemplated. Moreover, steps, or parts of the algorithm, may be implemented simultaneously or in parallel where appropriate.

It is also contemplated that the implementation of the components of the present invention can be done with any newly arising technology that may replace any of the above implementation technologies.

What is claimed is:

1. A method for treatment of a nervous system, the method comprising:
    inserting a flexible catheter including a drainage lumen into a cerebrospinal fluid space;
    draining cerebrospinal fluid through the drainage lumen in the catheter to decrease pressure in the nervous system;
    monitoring a functional status of thoracic spinal cord evoked potentials of the nervous system;
    monitoring a functional status of cervical spinal cord evoked potentials of the nervous system; and
    modifying the treatment of the nervous system to adjust for any change in the functional status of the thoracic spinal cord evoked potentials of the nervous system relative to the functional status of the cervical spinal cord evoked potentials of the nervous system.

2. The method of claim 1, wherein the treatment of the nervous system is for one or more of the following: trauma, tumor, hemorrhage, infection, spinal cord injury, increased intracranial/intrathecal pressure, ischemia, hypoxia, cerebral swelling, seizure, spinal cord swelling, aortic aneurysm surgery or endovascular treatment, aortic dissection surgery or endovascular treatment, cross clamping of aorta, scoliosis surgery, spine surgery, and cranial surgery.

3. The method of claim 1, wherein said modifying of the treatment of the nervous system comprises one or more of the following: adjusting temperature, adjusting intracranial pressure, adjusting spinal intrathecal/subdural pressure, adjusting blood pressure, adjusting said draining of the cerebrospinal fluid, adjusting cerebral perfusion pressure, adjusting blood flow, adjusting oxygenation, adjusting medication, adjusting anesthesia, and performing surgery.

4. The method of claim 1, wherein said draining of the cerebrospinal fluid comprises using one or more of the following: a valve that opens at a set pressure, an anti-reflux valve, an automated collection chamber that allows fluid drainage at a set pressure, a negative pressure suction collection chamber, and a drainage bag that allows fluid drainage at a set pressure based on a location of the drainage bag relative to anatomical landmarks.

5. A method for treatment of a nervous system, the method comprising:
    inserting a flexible catheter into a cerebrospinal fluid space, the flexible catheter including two lumens adapted to allow a fluid to circulate therein in a closed loop within the flexible catheter, and the flexible catheter being adapted to be connected to a device for cooling and circulating the fluid;
    cooling cerebrospinal fluid in the cerebrospinal fluid space with the flexible catheter to enable selective nervous system cooling;
    monitoring a functional status of thoracic spinal cord evoked potentials of the nervous system;
    monitoring a functional status of cervical spinal cord evoked potentials of the nervous system; and
    modifying the treatment of the nervous system to adjust for any change in the functional status of the thoracic spinal cord evoked potentials of the nervous system relative to the functional status of the cervical spinal cord evoked potentials of the nervous system.

6. The method of claim 5, wherein the treatment of the nervous system is for one or more of the following: trauma, tumor, hemorrhage, infection, spinal cord injury, increased intracranial/intrathecal pressure, ischemia, hypoxia, cerebral swelling, seizure, spinal cord swelling, aortic aneurysm surgery or endovascular treatment, aortic dissection surgery or endovascular treatment, cross clamping of aorta, scoliosis surgery, spine surgery, and cranial surgery.

7. The method of claim 5, wherein said modifying of the treatment of the nervous system comprises one or more of the following: adjusting a temperature of the fluid, adjusting body temperature, adjusting intracranial pressure, adjusting spinal intrathecal/subdural pressure, adjusting blood pressure, adjusting cerebrospinal fluid drainage, adjusting cerebral perfusion pressure, adjusting blood flow, adjusting oxygenation, adjusting medication, adjusting anesthesia, and performing surgery.

8. The method of claim 5, wherein the flexible catheter has a portion that is capable of expansion.

9. The method of claim 8, wherein the expansion of the flexible catheter comprises one or more of the following: lumen expansion, outer wall expansion, and one or more balloons.

10. A method for treatment of a nervous system, the method comprising:
providing a flexible catheter including two lumens adapted to allow a fluid to circulate therein in a closed loop within the flexible catheter, and a drainage lumen having one or more ports at a distal end of the flexible catheter which communicate with an environment outside the flexible catheter, the flexible catheter being adapted to be connected to a device for cooling and circulating the fluid;
inserting the flexible catheter into a spine to place a portion of the flexible catheter in a cerebrospinal fluid space;
cooling cerebrospinal fluid in the spine with the flexible catheter to enable selective cooling of a nervous system;
draining cerebrospinal fluid through the drainage lumen in the flexible catheter to decrease pressure in the nervous system;
monitoring a functional status of thoracic spinal cord evoked potentials of the nervous system;
monitoring a functional status of cervical spinal cord evoked potentials of the nervous system; and
modifying the treatment of the nervous system to adjust for any change in the functional status of the thoracic spinal cord evoked potentials of the nervous system relative to the functional status of the cervical spinal cord evoked potentials of the nervous system.

11. The method of claim 10, wherein the treatment of the nervous system is for one or more of the following: trauma, tumor, hemorrhage, infection, spinal cord injury, increased intracranial/intrathecal pressure, ischemia, hypoxia, cerebral swelling, seizure, spinal cord swelling, aortic aneurysm surgery or endovascular treatment, aortic dissection surgery or endovascular treatment, cross clamping of aorta, scoliosis surgery, spine surgery, and cranial surgery.

12. The method of claim 10, wherein said modifying of the treatment of the nervous system comprises one or more of the following: adjusting a temperature of the fluid, adjusting body temperature, adjusting intracranial pressure, adjusting spinal intrathecal/subdural pressure, adjusting blood pressure, adjusting said draining of the cerebrospinal fluid, adjusting cerebral perfusion pressure, adjusting blood flow, adjusting oxygenation, adjusting medication, adjusting anesthesia, and performing surgery.

13. The method of claim 10, wherein the flexible catheter has a portion that is capable of expansion.

14. The method of claim 13, wherein the expansion of the flexible catheter comprises one or more of the following: lumen expansion, outer wall expansion, and one or more balloons.

15. The method of claim 10, wherein said draining of the cerebrospinal fluid comprises using one or more of the following: a valve that opens at a set pressure, an anti-reflux valve, an automated collection chamber that allows fluid drainage at a set pressure, a negative pressure suction collection chamber, and a drainage bag that allows fluid drainage at a set pressure based on a location of the drainage bag relative to anatomical landmarks.

16. A method for treatment of a nervous system, the method comprising:
providing a flexible catheter including two lumens adapted to allow a fluid to circulate therein in a closed loop within the flexible catheter, and a drainage lumen having one or more ports which communicate through the drainage lumen with an environment outside the flexible catheter, the flexible catheter being adapted to be connected to a device for cooling and circulating the fluid;
inserting the flexible catheter into the nervous system to place a portion of the flexible catheter in a cerebrospinal fluid space;
cooling cerebrospinal fluid with the flexible catheter to enable selective cooling of the nervous system;
draining cerebrospinal fluid through the drainage lumen in the flexible catheter to maintain a set pressure in the nervous system with positioning of a collection chamber based on anatomical landmarks; and
modifying the treatment of the nervous system to adjust for any change in a functional status of thoracic spinal cord evoked potentials of the nervous system relative to a functional status of a cervical spinal cord evoked potentials of the nervous system.

17. The method of claim 16, wherein the anatomical landmarks include one of the following: ear, external auditory meatus, and shoulder.

18. The method of claim 16, wherein said draining of the cerebrospinal fluid comprises using one or more of the following: a valve that opens at a set pressure, an anti-reflux valve, an automated collection chamber that allows fluid drainage at a set pressure, a negative pressure suction collection chamber, feedback control of an amount of fluid drainage based at a set pressure, and a drainage bag.

* * * * *